United States Patent
Ahluwalia et al.

(10) Patent No.: US 9,226,931 B2
(45) Date of Patent: *Jan. 5, 2016

(54) TOPICAL TREATMENT FOR CHEMOTHERAPY INDUCED EYELASH LOSS OR HYPOTRICHOSIS USING PROSTAMIDE F2 ALPHA AGONISTS

(71) Applicant: Allergan, Inc., Irvine, CA (US)

(72) Inventors: Gurpreet Ahluwalia, Orange, CA (US); Frederick C. Beddingfield, Pacific Palisades, CA (US); Sydney G. Edwards, Aliso Viejo, CA (US); Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/199,402

(22) Filed: Mar. 6, 2014

(65) Prior Publication Data

US 2014/0187642 A1    Jul. 3, 2014

Related U.S. Application Data

(63) Continuation of application No. 13/738,732, filed on Jan. 10, 2013, now Pat. No. 8,758,733, which is a continuation-in-part of application No. 13/937,512, filed on Jul. 9, 2013, now Pat. No. 8,926,953, which is (Continued)

(51) Int. Cl.
*A61K 8/00* (2006.01)
*A61K 31/5575* (2006.01)
(Continued)

(52) U.S. Cl.
CPC ............ *A61K 31/5575* (2013.01); *A61K 8/42* (2013.01); *A61K 8/4953* (2013.01); *A61K 8/63* (2013.01); *A61K 9/0014* (2013.01); *A61K 31/165* (2013.01); *A61K 31/438* (2013.01); *A61K 31/506* (2013.01); *A61K 31/557* (2013.01); *A61K 31/558* (2013.01); *A61Q 1/10* (2013.01); *A61Q 7/00* (2013.01)

(58) Field of Classification Search
CPC .................................................. A61K 2800/00
See application file for complete search history.

(56) References Cited

U.S. PATENT DOCUMENTS 3,382,247 A    5/1968    Anthony et al.
3,644,363 A    2/1972    Hyun Koo Kim
(Continued)

FOREIGN PATENT DOCUMENTS

AU    2008203212    10/2008
AU    2010227111    11/2010
(Continued)

OTHER PUBLICATIONS

U.S. Appl. No. 90/009,431, filed Mar. 10, 2009, Murray Johnstone.
(Continued)

*Primary Examiner* — Paul Dickinson
(74) *Attorney, Agent, or Firm* — Lorenz Siddiqi

(57) ABSTRACT

The present invention is directed to compositions and methods for the treatment of post-chemotherapeutic hypotrichosis. More specifically, the present invention is directed to the use of compositions comprising bimatoprost for the treatment of post-chemotherapeutic hypotrichosis which may be applied before, during and after receiving chemotherapeutic treatment.

20 Claims, 10 Drawing Sheets

Example of the Effect of Bim 0.03% on Eyelash Growth Compared to Vehicle – Post-chemotherapy population

Related U.S. Application Data a continuation-in-part of application No. 13/441,783, filed on Apr. 6, 2012, now Pat. No. 8,632,760, which is a continuation of application No. 13/356,284, filed on Jan. 23, 2012, now Pat. No. 8,263,054, which is a continuation of application No. 12/425,933, filed on Apr. 17, 2009, now Pat. No. 8,298,518, which is a continuation of application No. 11/943,714, filed on Nov. 21, 2007, now Pat. No. 8,038,988, which is a continuation of application No. 11/805,122, filed on May 22, 2007, now Pat. No. 8,101,161, which is a continuation of application No. 10/345,788, filed on Jan. 15, 2003, now Pat. No. 7,351,404.

(60) Provisional application No. 60/354,425, filed on Feb. 4, 2002, provisional application No. 61/611,920, filed on Mar. 16, 2012, provisional application No. 61/584,877, filed on Jan. 10, 2012.

(51) Int. Cl.

| | | |
|---|---|---|
| A61K 31/165 | (2006.01) | |
| A61K 31/506 | (2006.01) | |
| A61K 31/438 | (2006.01) | |
| A61K 8/42 | (2006.01) | |
| A61Q 7/00 | (2006.01) | |
| A61K 31/557 | (2006.01) | |
| A61K 31/558 | (2006.01) | |
| A61K 8/49 | (2006.01) | |
| A61Q 1/10 | (2006.01) | |
| A61K 8/63 | (2006.01) | |
| A61K 9/00 | (2006.01) | |

(56) References Cited

U.S. PATENT DOCUMENTS

| | | |
|---|---|---|
| 4,128,577 A | 12/1978 | Nelson |
| 4,139,619 A | 2/1979 | Chidsey |
| 4,311,707 A | 1/1982 | Birnbaum et al. |
| 4,543,353 A | 9/1985 | Faustini et al. |
| 4,596,812 A | 6/1986 | Chidsey et al. |
| 4,599,353 A | 7/1986 | Bito |
| 4,812,457 A | 3/1989 | Narumiya et al. |
| 4,839,342 A | 6/1989 | Kaswan |
| 4,883,581 A | 11/1989 | Dickakian |
| 4,888,354 A | 12/1989 | Chang et al. |
| 4,889,845 A | 12/1989 | Ritter et al. |
| 4,952,581 A | 8/1990 | Bito et al. |
| 4,968,812 A | 11/1990 | Wang et al. |
| 5,001,153 A | 3/1991 | Ueno et al. |
| 5,194,429 A | 3/1993 | Ueno et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,321,128 A | 6/1994 | Stjernschantz et al. |
| 5,352,708 A | 10/1994 | Woodward et al. |
| 5,422,368 A | 6/1995 | Stjernschantz et al. |
| 5,422,369 A | 6/1995 | Stjernschantz et al. |
| 5,431,881 A | 7/1995 | Palacios |
| 5,474,979 A | 12/1995 | Ding et al. |
| 5,480,900 A | 1/1996 | DeSantis et al. |
| 5,508,303 A | 4/1996 | Isogaya et al. |
| 5,510,383 A | 4/1996 | Bishop et al. |
| 5,545,655 A | 8/1996 | Friedlander et al. |
| 5,578,618 A | 11/1996 | Stjernschantz et al. |
| 5,578,643 A | 11/1996 | Hanson et al. |
| 5,607,978 A | 3/1997 | Woodward et al. |
| 5,688,819 A | 11/1997 | Woodward |
| 5,698,733 A | 12/1997 | Hellberg et al. |
| 5,773,472 A | 6/1998 | Stjernschantz et al. |
| 5,789,244 A | 8/1998 | Heidrun et al. |
| 6,025,392 A | 2/2000 | Selliah et al. |
| 6,124,344 A | 9/2000 | Burk |
| 6,160,129 A | 12/2000 | Burk |
| 6,203,782 B1 | 3/2001 | Eliaz et al. |
| 6,232,344 B1 | 5/2001 | Feng et al. |
| 6,254,860 B1 | 7/2001 | Garst |
| 6,258,844 B1 | 7/2001 | Garst et al. |
| 6,262,105 B1 | 7/2001 | Johnstone |
| 6,350,442 B2 | 2/2002 | Garst |
| 6,403,649 B1 | 6/2002 | Woodward |
| 6,441,047 B2 | 8/2002 | DeSantis |
| 7,351,404 B2 | 4/2008 | Woodward et al. |
| 7,368,436 B2 | 5/2008 | Gleave et al. |
| 7,388,029 B2 | 6/2008 | DeLong et al. |
| 7,514,474 B1 | 4/2009 | Lipkin et al. |
| 8,038,988 B2 | 10/2011 | Woodward et al. |
| 8,101,161 B2 | 1/2012 | Woodward et al. |
| 8,298,518 B2 | 10/2012 | Woodward et al. |
| 8,926,953 B2 | 1/2015 | Woodward et al. |
| 8,986,715 B2 | 3/2015 | Woodward et al. |
| 2002/0044953 A1 | 4/2002 | Michelet et al. |
| 2002/0103255 A1 | 8/2002 | Hellberg et al. |
| 2002/0172693 A1 | 11/2002 | DeLong et al. |
| 2003/0083381 A1 | 5/2003 | Kumagai et al. |
| 2003/0147823 A1 | 8/2003 | Woodward et al. |
| 2003/0199590 A1 | 10/2003 | Cagle et al. |
| 2004/0052760 A1 | 3/2004 | Michelet et al. |
| 2005/0222232 A1 | 10/2005 | Delong et al. |
| 2007/0160562 A1 | 7/2007 | Brinkenhoff |
| 2008/0070988 A1 | 3/2008 | Woodward et al. |
| 2008/0275118 A1 | 11/2008 | Shaw et al. |
| 2009/0018204 A1 | 1/2009 | Brinkenhoff |
| 2009/0270392 A1 | 10/2009 | Old et al. |
| 2011/0002866 A1 | 1/2011 | Lubit et al. |
| 2011/0112198 A1 | 5/2011 | Gore et al. |
| 2014/0194450 A1 | 7/2014 | Ahluwalia et al. |
| 2014/0221493 A1 | 8/2014 | Ahluwalia et al. |

FOREIGN PATENT DOCUMENTS

| | | |
|---|---|---|
| CA | 1208560 | 7/1986 |
| CA | 2144967 | 3/1994 |
| CA | 2174655 | 4/1995 |
| CA | 1339132 | 7/1997 |
| EP | 0170258 | 2/1986 |
| EP | 0249194 | 12/1987 |
| EP | 0308135 | 3/1989 |
| EP | 0639563 | 2/1995 |
| EP | 2802331 | 11/2014 |
| FR | 2239458 | 7/1973 |
| JP | S49-069636 | 7/1974 |
| JP | 61-218510 | 9/1986 |
| JP | H05-0331025 | 12/1993 |
| JP | H09-295921 | 11/1997 |
| JP | 10-287532 | 10/1998 |
| WO | 89-03384 | 4/1989 |
| WO | 95-11003 | 4/1995 |
| WO | 97-31895 | 9/1997 |
| WO | 98-33497 | 8/1998 |
| WO | 99-12895 | 3/1999 |
| WO | 00-54810 | 9/2000 |
| WO | 01-74307 | 10/2001 |
| WO | 01-74315 | 10/2001 |
| WO | 2007-143568 | 12/2007 |
| WO | 2009-011744 | 1/2009 |
| WO | 2011-119748 | 9/2011 |
| WO | 2012068515 | 5/2012 |
| WO | 2013106565 | 7/2013 |

OTHER PUBLICATIONS

U.S. Appl. No. 90/009,430, filed Mar. 15, 2009, David Woodward.

Abramovitz, Mark et al, The Utilization of Recombinant prostanoid Receptors to Determine the Affinities and Selectivities of Prostaglandins and Related Analogs, Biochimica et Biophysica Acta, 2000, 285-293, 1483.

Abramovitz, Mark, Cloning and Expressing of a cDNA for the Human prostanoid FP Receptor, Journal of Biological Chemistry, 1994, 2632-2636, 269(4).

(56) References Cited

OTHER PUBLICATIONS

Adis Data Information, ZD 6416, 2003.
Adis, Alprostadil (NexMed) Alprox-TDTM, BefarTM, FemproxTM, Prostaglandin E1 (NewMed), Adis R & D Profile, 1999, 413-414, 2(6), Adis International Limited.
Al-Sereiti, M.R., Pharmacology of Rosemary (Rosmarinus Officinalis Linn.) and its Therapeutic Potentials, Indian Journal of Experimental Biology, 1999, 124-130, 37.
Allergan Clinical Study Report, 192024-008, 2000.
Allergan, Inc., Dermatologic and Ophthalmic Drugs Advisory Committee Briefing Document for Bimatoprost Solution 0.03%, Dermatologic and Ophthalmic Drugs Advisory Committee Briefing Document for Bimatoprost Solution 0.03%, Oct. 29, 2008, 1-108.
Alm, Albert et al, Effects on Intraocular Pressure and Side Effects of 0.005% Latanoprost Applied Once Daily, Evening or Morning, Ophthalmology, 1995, 1743-1752, 102.
Alm, Albert et al, Phase III Latanoprost Studies in Scandinavia, the United Kingdom and the United States, Survey of Ophthalmology, Feb. 1997, S105-S110, 41(2).
Alm, Albert et al, Uveoscleral Outflow—A Review, Experimental Eye Research, 2009, 760-768, 88(4).
Alm, Albert, The Potential of Prostaglandin Derivates in Glaucoma Therapy, Current Opinion in Ophthalmology, 1993, 44-50, 4(11).
Audoly, Laurent et al, Identification of Specific EP Receptors Responsible for the Hemodynamic Effects of PGE2, Am. J. Physiol., 1999, H924-H930, 277.
Badawy, Sherif et al, Salt Selection for Pharmaceutical Compounds, Preformulation in Solid Dosage Form Development (Informa Healthcare), 2008, 63-80, Chapter 2.3, Adeyeyem, Moji, ed.
Bartmann, W., Synthesis and Biological Activity, Luteolytic Prostaglandins, Feb. 1979, 301-311, 17(2).
Bastin, Richard et al, Salt Selection and Optimisation Procedures for Pharmaceutical New Chemical Entities, Organic Process Research & Development, 2000, 427-435, 4.
Bean, Gerald, Commercially Available Prostaglandin Analogs for the Reduction of Intraocular Pressure: Similarities and Differences, Survey of Ophthalmology, 2008, S69-S84, 53 (Supp. 1).
Beisecker, Analee et al, Side Effects of Adjuvant Chemotherapy: Perceptions of Node-Negative Breast Cancer Patients, Psycho-Oncology, 1997, 85-93, 6.
Berge, Stephen M., Pharmaceutical Salts, Journal of Pharmaceutical Sciences, Jan. 1977, 1-19, 66 (1), US.
Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.
Bito, L.Z. et al, Long-Term Maintenance of Reduced Intraocular Pressure by Daily or Twice Daily Topical Application of Prostaglandins to Cat or Rhesus Monkey Eyes, Investigative Ophthalmology & Visual Science, 1983, 312-319, 24(3).
Bito, Laszlo, A new approach to the medical management of glaucoma, from the bench to the clinic, and beyond, Investigative Ophthalmology & Visual Science, 2001, 1126-1133, 42(6), The Proctor Lecture.
Block, Lawrence, Medicated Applications, Remington's Pharmaceutical Sciences, 1985, 1567-1578, 17th Edition, Chapter 88.
Botchkarev, Vladimir, Molecular Mechanisms of Chemotherapy-Induced Hair Loss, JID Symposium Proceedings, 2003, 72-75, 8.
Brandt, James et al, Comparison of Once- or Twice-Daily Bimatoprost with Twice-Daily Timolol in Patients with Elevated IOP, American Academy of Ophthalmology, 2001, 1023-1031, 108(6).
Brandt, James, PA022 Phase III, 3-month Comparison in Timolol with AGN-192024: A New Ocular Hypotensive Lipid for Glaucoma Management, Presented at 2000 Am. Acad. Ophthalmology, Ann. Mtg., Oct. 23, 2000, 1 Page.
Brubaker, Richard et al, Effects of AGN 192024, a new Ocular Hypotensive Agent, on Aqueous Dynamics, American journal of Ophthalmology, 2001, 19-24, 131(1).
Brundy, Gordon, Synthesis of 17-Phenyl-18, 19, 20-Trinorprostaglandins I. The PG1 Series, Prostaglandins, 1975, 1-4, 9(1).
Business Wire, Phase III Lumigan, AGN-192024—Data Presented at American Academy of Ophthalmology, American Academy of Ophthalmology, 2000, 1-3, Retrieved Dec. 14, 2010.
Cadet, Patrick et al, Molecular Identification and Functional Expression of µ3, a Novel Alternatively Spliced Variant of the Human µ Opiate Receptor Gene, J. Immunol., 2003, 5118-5123, 170.
Camras, Carl B. et al, Bimatoprost, the Prodrug of a Prostaglandin Analogue, Br J Ophthalmol, 2008, 862-863, 92.
Camras, Carl B. et al, Comparison of Latanoprost and Timolol in Patients with Ocular Hypertension and Glaucoma, Ophthalmology, 1996, 138-147, 103(1).
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg.
Camras, Carl B. et al, Latanoprost, a prostaglandin Analog, for Glaucoma Therapy, Ophthalmology, 1996, 1916-1924, 103(11).
Camras, Carl B. et al, Multiple Dosing of Prostaglandin F2α or Epinephrine on Cynomolgus Monkey Eyes, Investigative Ophthalmology & Visual Science, Sep. 1988, 1428-1436, 29(9).
Camras, Carl B. et al, Multiple Dosing of Prostaglandin F2α or Epinephrine on Cynomolgus Monkey Eyes, Investigative Ophthalmology & Visual Science, 1987, 463-469, 28(3).
Camras, Carl B. et al, Multiple Dosing of Prostaglandin F2α or Epinephrine on Cynomolgus Monkey Eyes, Investigative Ophthalmology & Visual Science, 1987, 921-926, 28(6).
Camras, Carl B. et al, Reduction of Intraocular Pressure in Normal and Glaucomatous Primate (*Aotus trivirgatus*) Eyes by Topically Applied Prostaglandin F2α, Current Eye Research, 1981, 205-209, 1 (4).
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
CAS RN 155206-00-1 May 20, 1994.
Cayatte, Antonio et al, The Thromboxane A2 Receptor Antagonist, S18886, Decreases atherosclerotic Lesions and serum Intracellular Adhesion Molecule-1 in the Apo E Knockout Mouse, 71st Scientific Sessions, 1998, I-115 (Abstract), 98(17).
Chen, June et al, AGN 191219: A Neutral Prostaglandin F2n (PGF2n) Analog That Lacks the Mitogenic and Uterotonic Effects Typical of FP Receptor Agonists, Glaucoma, Anatomy & Pathology, Physiology & Pharmacology, 1999, 3562-B420, 40(4).
Chen, June et al, Replacement of the Carboxylic Acid Group of Prostaglandin F2α (PGF2α) with Certain Non-Ionizable Substituents Results in Pharmacologically Unique Ocular Hypotensive Agents, 11th Intl Conf. Advances Prostaglandin & Leukotriene Res.: Basic Sci. & New Clinical Applications—Abstract Book, 2000, 1 page.
Chen, June et al, Studies on the Pharmacology of Prostamide F2α, A Naturally Occurring Substance, Brit. J. Pharmacology, 2001, 63P, 133.
Chyun, Yong et al, Stimulation of Bone Formation by Prostaglandin E2, Prostaglandins, 1984, 97-103, 27(1).
Clissold, D., The Potential for Prostaglandin Pharmaceuticals, Lipids in Health and Nutrition, 1999, 115-129, 244, The Royal Society of Chemistry.
Cohen, Joel, Enhancing the Growth of Natural Eyelashes: The Mechanism of Bimatoprost-Induced Eyelash Growth, Dermatol Surg, 2010, 1361-1371, 36(9).
Coleman, Robert et al, Prostanoids and Their Receptors, Comprehensive Medicinal Chemistry, 1990, 643-714, 3.
Coleman, Robert, VIII. International union of Pharmacology Classification of Prostanoid Receptors: Properties, Distribution, and Structure of the Receptors and Their Subtypes, The American Society for Pharmacology and Experimental Therapeutics, 1994, 205-229, 26(2).
Collins, Paul et al, Synthesis of Therapeutically Useful Prostaglandin and Prostacyclin Analogs, Chem. Rev., 1993, 1533-1564, 93.

(56) References Cited

OTHER PUBLICATIONS

Corsini, A. et al, (5Z)-Carbacyclin Discriminates Between Prostacyclin-Receptors Coupled to Adenylate Cyclase in Vascular Smooth Muscle and Platelets, Br. J. Pharmac., 1987, 255-261, 90.
Cowley, Lorraine et al, How Women Receiving Adjuvant Chemotherapy for Breast Cancer Cope With Their Treatment: a Risk Management Perspective, Journal of Advanced Nursing, 2000, 314-321, 31(2).
Cox, Colin et al, Protein Fabrication Automation, Protein Science, 2007, 379-390, 16.
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Darnell, J., Cell-to-Cell Signaling: Hormones and Receptors, Molecular Cell Biology, 1990, 738-743, vol. 82, Darnell, J., Lidish, H., Baltimore, D., Eds., New York, New York.
Davies, Sean, Hydrolysis of Bimatoprost (Lumigan) to Its Free Acid by Ocular Tissue In Vitro, Journal of Ocular Pharmacology and Therapeutics, 2003, 45-54, 19(1).
De Asua, L Jimenez et al, The Stimulation of the Initiation of DNA Synthesis and Cell Division in Swiss Mouse 3T3 Cells by Prostaglandin F2α Requires Specific Functional Groups in the Molecule, J. Biol. Chemistry, 1983, 8774-8780, 256(14).
Dean, T.R. et al, Improvement of Optic Nerve Head Blood Flow After One-Week Topical Treatment with Travoprost (AL06221) in the Rabbit, Investigative Ophthalmology & Visual Science, Mar. 15, 1999, 2688-B563, 40(4).
Del Toro, F. et al, Characterization of Prostaglandin E2 Receptors and Their Role in 24,25-(OH)2D3-Mediated Effects on Resting Zone Chondrocytes, Journal of Cellular Physiology, 2000, 196-208, 182.
Delong, Mitchell, Prostaglandin Receptor Ligands: Recent Patent Activity, IDrugs, 2000, 196-208, 3(9).
Depperman, William, Up-To-Date Scalp Tonic, Book Reviews, 1970, 1115, 283(20).
Dirks, Monte et al, Efficacy and Safety of the Ocular Hypotensive Lipid™ 192024 in Patients with Elevated IOP: A 30-Day Comparison with Latanoprost, Investigative Ophthalmology & Visual Science, Mar. 15, 2000, S514, 41(4).
Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).
Easthope, Stephanie et al, Topical Bimatoprost, Drug Aging, 2002, 231-248, 19(3).
Eisenberg, Dan et al, A Preliminary Risk-Benefit Assessment of Latanoprost and Unoprostone in Open-Angle Glaucoma and Ocular Hypertension, Drug Safety, 1999, 505-514, 20(6).
Ellis, Cathy et al, Metabolism of Prostaglandin D2 in the Monkey, The Journal of Biological Chemistry, 1979, 4152-4163, 254(10).
Enyedi, Laura et al, The Effectiveness of Latanoprost for the Treatment of Pediatric Glaucoma, J AAPOS, 1999, 33-39, 3(1).
Fagien, Steven, Management of Hypotrichosis of the Eyelashes: Focus on Bimatoprost, Clinical, Cosmetic and Investigational Dermatology, 2010, 39-48, 3.
Fagot, Dominique et al, Mitogenic Signaling by Prostaglandins in Chemically Transformed Mouse Fibroblasts: Comparison with Phorbol Esters and Insulin, Endocrinology, 1993, 1729-1734, 132(4).
Fall, P.M., Inhibition of Collagen Synthesis by Prostaglandins in the Immortalized Rat Ostroblastic Cell Line Pyla: Structure-Activity Relations and Signals Transduction Mechanisms, J. Bone Miner Res., 1994, 1935-1943, 9(12).
Faulkner, Robert, Aqueous Humor Concentrations of Bimatoprost Free Acid, Bimatoprost and Travoprost Free Acid in Cataract Surgical Patients administered Multiple Topical Ocular Doses of LUMIGAN or TRAVATAN, Journal of Ocular Pharmacology and Therapeutics, 2010, 147-156, 26(2).
FDA Approves Two New intraocular Pressure Lowering Drugs for the Management of Glaucoma, Mar. 16, 2001, FDA News.
FDA Label for Approved NDA 22-184 of Lumigan 0.01% and Lumigan 0.03%, Aug. 31, 2010.
Fiscella, Richard, Peek into the Drug Pipeline, Review of Optometry Online, Jan. 15, 2001, 5 pages.
Fitzpatrick, F.A., Separation of Prostaglandins and Thromboxanes by Gas Chromatography with Glass Capillary Columns, Analytical Chemistry, 1978, 47-52, 50(1).
Flisiak, Robert et al, Effect of Misoprostol on the Course of Viral Hepatitis B, Hepato-Gastroenterology, 1997, 1419-1425, 44.
Freedman, Tovia et al, Social and Cultural Dimensions of Hair Loss in Women Treated for Breast Cancer, Cancer Nursing, 1994, 334-341, 17(4).
Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).
Funk, Colin et al, Cloning and Expression of a cDNA for the Human Prostaglandin E Receptor EP1 Subtype*, The Journal of Biological Chemistry, Dec. 15, 1993, 26767-26772, 268(35).
Gandolfi, Stefano, Three-month Comparison of Bimatoprost and Latanoprost in Patients With Glaucoma and Ocular Hypertension, Adv. Ther, 2001, 110-121, 18.
Garadi, R et al, Travoprost: A New Once-Daily Dosed Prostaglandin for the Reduction of Elevated Intraocular Pressure, Investigative Ophthalmology & Visual Science, 1999, 4378-B181, Abstract.
Geng, Ling et al, Misoprostol, A PGE1 Analog That is Radioprotective for Murine Intestine and Hair, Induces Widely Different Cytokinetic Changes in These Tissues, The Journal of Investigative Dermatology, 1996, 858, 106(4).
Geng, Ling et al, Topical or Systemic 16,16 dm Prostaglandin E2 or WR-2721 (WR-1065) Protects Mice From Alopecia After Fractionated Irradiation, Int. J. Radiat. Biol., 1992, 533-537, 61(4).
Gerth, Jeff et al, Drug Makers Reap Profits on Tax-Backed Research, Apr. 23, 2000, 10 pages, New York Times.
Giuffre, Giuseppe, The Effects of Prostaglandin F2α in the Human Eye, Graefe's Archive Clin. & Exper. Ophthal., 1985, 139-141, 222.
Griffin, Brenda et al, AL-8810: A Novel Prostaglandin F2α Analog with Selective Antagonist Effects at the Prostaglandin F2α (FP) Receptor, Journal of Pharmacology and Experimental Therapeutics, 1999, 1278-1284, 290(3).
Grow (Verb) Definition, Merriam Webster's Dictionary, Retrieved from http://www.merriam-webster.com/dictionary/growing on Jul. 9, 2012.
Hall, Alistair et al, Clinprost Tijin, Current Opinion in Cardiovascular, Pulmonary & Renal Investigational Drugs, 1999, 605-610, 1(5).
Hallinan, Ann et al, Aminoacetyl Moiety as a Potential Surrogate for Diacylhydrazine Group of SC -51089, a Potent PGE2 Antagonist, and Its Analogs, J Med Chem, 1996, 609-613, 39.
Hanson, W R et al, 16,16 dm Prostaglandin2 Protects From Acute Radiation-Induced Alopecia in Mice, Clinical Research, 1988, 906A, 36(6).
Hanson, W R et al, Subcutaneous or Topical Administration of 16,16 Dimethyl Prostaglandin E2 Protects From Radiation-Induced Alopecia in Mice, Int. J. Radiation Oncology Biol. Phys., 1992, 333-337, 23.
Hartke, J.R. et al, Prostanoid FP Agonists Build Bone in the Ovariectomized Rat, Prostanoid FP Agonists Build Bone in the Ovariectomized Rat, 1999, S207.
Hayashi, Masaki et al, Prostaglandin Analogues Possessing Antinidatory Effects. 1. Modification of the ω Chain, J. Med. Chem., 1980, 519-524, 23.
Hecker, Markus et al, Studies on the Interaction of Minoxidil with Prostacyclin Synthase in Vitro, Biochemical Pharmacology, 1988, 3363-3365, 37(17).
Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).
Higginbotham et al., "One-Year, Randomized Study Comparing Bimatoprost and Timolol in Glaucoma and Ocular Hypertension", Archives of Opthalmology, Oct. 2002, 1286-1293, 120 (10), US.
Houssay, Alerto, Effects of Prostaglandins Upon Hair Growth in Mice, Acta Physiol. Latinoam., 1976, 186-191, 26.
Huang, A. et al, Different Modes of Inhibition of Increase in Cytosolic Calcium and Aggregation of Rabbit Platelets by Two Thromboxane A2 Antagonists, Asia Pacific Journal of Pharmacology, 1994, 163-171, 9.

(56) References Cited

OTHER PUBLICATIONS

Hulan, H.W. et al, The Development of Dermal Lesions and Alopecia in Male Rats Fed Rapeseed Oil, Canadian Journal of Physiology and Pharmacology, 1976, 1-6, 54(1).
Hulan, H.W. et al, The Effect of Long-Chain Monoenes on Prostaglandin E2 Synthesis by Rat Skin, Lipids, 1977, 604-609, 12(7).
Hunt, Nigel et al, The Psychological Impact of Alopecia, BMJ, Oct. 2005, 951-953, 331.
Ichikawa, A. et al, Molecular Aspects of the Structures and Functions of the Prostaglandin E Receptors, J. Lipid Mediators Cell Signalling, 1996, 83-87, 14.
Informa UK Ltd., AGN-192024, 2006, 3 Pages.
Inoue, Hironishi, Thromboxane A2 receptor antagonists, Oct. 1996, 1221-1225, 32(10), Pharmaceutical Society of Japan.
J Am Pharm Assoc—, Agents for Glaucoma, New Drugs of 2001, 2001, 4 pages, 42(2), Journal of the American Pharmaceutical Association, http://www.edscape.com/viewarticle/436631__22, US.
Jakobsson, Per-Johan et al, Membrane-Associated Proteins in Eicosanoid and Glutathione Metabolism (MAPEG), American Journal of Respiratory and Critical Care Medicine, 2000, S20-S24, 161.
Jimenez, J.J. et al, Stimulated Monocyte-Conditioned Media Protect From Cytosine Arabinoside-Induced Alopecia in Rat, Friday Afternoon Subspecialty Meetings, 1990, 973A.
Johnstone, M.A., Brief Latanoprost RX Induces Hypertrichosis, Glaucoma Clinical Pharmacology II Poster Presentation, 1998, S258, 39(4).
Johnstone, Murray, Hypertrichosis and Increased Pigmentation of Eyelashes and Adjacent Hair in the Region of the Ipsilateral Eyelids of Patients Treated With Unilateral Topical Latanoprost, American Journal of Ophthalmology, 1997, 544-547, 124(4).
Jordan, B.A. et al, G-Protein-Coupled Receptor Heterodimerization Modulates Receptor Function, Nature, Jun. 17, 1999, 697-700, 399(6737).
Karim, S.M. et al, Prostaglandins and Human Respiratory Tract Smooth Muscle: Structure Activity Relationship, Advances in Prostaglandin and Thromboxane Research, 1980, 969-980, 7.
Karuss, Achim et al, Evidence for Human Thromboxane Receptor Heterogeneity Using a Novel Series of 9,11—Cyclic Carbonate Derivatives of Prostaglandin F2α, British Journal of Pharmacology, 1996, 1171-1180, 117.
Katz, L.J. et al, Comparison of Human Ocular Distribution of Bimatoprost and Latanoprost, 2010, P450.
Kaufman, Paul, Effects of Intracamerally Infused Prostaglandins on Outflow Facility in Cynomolgus Monkey Eyes with Intact or Retrodisplaced Ciliary Muscle, Experimental Eye Research, 1986, 819-827, 43.
Kende, Andrew et al, Prostaglandin Phosphonic Acids Through Homolytic Halodecarboxylation of Prostaglandins F1α and F2α, Tetrahedron Letters, 1999, 8189-8192, 40.
Kerstetter, J.R. et al, Prostaglandin F2α-1-lsopropylester Lowers Intraocular Pressure Without Decreasing Aqueous Humor Flow, American Journal of Ophthalmology, 1988, 30-34, 105.
Kiriyama, Michitaka et al, Ligand Binding Specificities of the Eight Types and Subtypes of the Mouse Prostanoid Receptors Expressed in Chinese Hamster Ovary Cells, British Journal of Pharmacology, 1997, 217-224, 122.
Kluender, Harold et al, The Synthesis of Dimethylphosphonoprostaglandin Analogs, Prostaglandins and Medicine, 1979, 441-444, 2.
Kvedar, Joseph et al, Topical Minoxidil in the Treatment of Male Pattern Alopecia, Pharmacotherapy, 1987, 191-197, 7(6).
Lachgar, S. et al, Effect of VEGF and Minoxidil on the Production of Arachidonic Acid Metabolites by Cultured Hair, Dermal Papilla Cells, Eur. J. Dermatol, 1996, 365-368, 6.
Lachgar, S. et al, Hair Dermal Papilla Cell Metabolism is Influenced by Minoxidil, Fundamental & Clinical Pharmacology, 1997, 178, 11(2).
Lachgar, S. et al, Modulation by Minoxidil and VEGF of the Production of Inflammatory Mediators by Hair Follicle Dermal Papilla Cells, Groupe de Rocherche Dermatologique, 1995, 161, 104(1).
Lambert, Joseph, Clinical Study Report, A Multicenter, Double-Masked, Randomized, Parallel, 3-Month study (with Treatment Extended to 1 year) of the Safety and Efficacy of AGN 192024 0.03% Ophthalmic Solution Administered Once-Daily or Twice-daily Compared with Timolol 0.5% Ophthalmic Solution Administered Twice-Daily in Subjects with Glaucoma or Ocular Hypertension, Study No. 192024-009, Phase 3, 1998, 34 pages.
Lardy, C. et al, Antiaggregant and Antivasospastic Properties of the New Thromboxane A2 Receptor Antagonist Sodium 4-[[1-[[[(4 Chlorophenyl)sulfony]amino]methyl]cyclopentyl]methyl]benzeneacetate, Arzneim.-Forsch./Drug Res., 1994, 1196-1202, 44(11).
Law, Simon, Bimatoprost in the Treatment of Eyelash Hypotrichosis, Clinical Ophthalmology, 2010, 349-358, 4.
Lee, Ping-Yu et al, The Effect of Prostaglandin F2α on Intraocular Pressure in Mormotensive Human Subjects, Investigative Ophthalmology & Visual Science, Oct. 1988, 1474-1477, 29(10).
Lee, Vincent et al, Improved Ocular Drug Delivery with Prodrugs, Prodrugs: Topical and Ocular Drug Delivery, 1992, 221-297, Kenneth Sloan Edition.
Lemieux, Julie et al, Chemotherapy-Induced Alopecia and Effects on Quality of Life Among Women With Breast Cancer: a Literature Review, Psycho-Oncology, 2008, 317-328, 17.
Liang, Y. et al, Identification and Pharmacological Characterization of the Prostaglandin FP Receptor and FP Receptor Variant Complexes, Br. J. Pharmacol., 2008, 1079-1093, 154.
Liljebris, Charlotta et al, Derivatives of 17-Phenyl-18,19,20-trinorprostaglandin F2α Isopropyl Ester: Potential Antiglaucoma Agents, J. Med. Chem., 1995, 289-304, 38.
Ling, Geng et al, 16,16 dm Prostaglandin E2 Protects Mice From Fractionated Radiation-Induced Alopecia, Clinical Research, 1990, 858A, 38(3).
Lumigan 6-Month Phase 3 Data Presented at American Glaucoma Society Meeting, Mar. 2, 2001, 4 pages, Business Wire.
Lumigan Package Insert, Mar. 2001, 6 pages, NDA 21-275.
Lundy, M.W. et al, Restoration of Cancellous Architecture and Increased Bone Strength in Aged Osteopenic Rats Treated with Fluprostenol, 21st Annual Meeting of the American Society for Bone and Mineral Research, 1999, S401.
Luoma, Minna-Li Isa et al, The Meaning of Quality of Life in Patients Being Treated for Advanced Breast Cancer: a Qualitative Study, Psycho-Oncology, 2004, 729-739, 13.
Maddox, Yvonne et al, Amide and I-amino Derivatives of F Prostaglandins as Prostaglandin Antagonists, Nature, Jun. 15, 1978, 549-552, 273.
Malkinson, Frederick et al, Prostaglandins Protect Against Murine Hair Injury Produced by Ionizing Radiation of Doxorubicin, J. Invest. Dermatol., 1993, 135S-137S, 101.
Mansberger, Steven et al, Eyelash Formation Secondary to Latanoprost Treatment in a Patient With Alopecia, Arch. Opthalmol., 2000, 718-719, 118.
Maruyama, Takayuki et al, EP1 Receptor Antagonists Suppress Tactile Allodynia in Rats, Prostaglandins & Other Lipid Mediators, 1999, 217(Abstract), 59.
Matsumura, H. et al, Brain and Neuroscience, 1998, 79-89.
Maw, Graham, Chapter 8. Pharmacological Therapy for the Treatment of Erectile Dysfunction, Annual Reports in Medicinal Chemistry, 1999, 71-80.
Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).
McCullough, Peter et al, Ridogrel Janssen, Current Opinion in Anti-inflammatory & Immunodulatory Investigational Drugs, 1999, 265-276, 1(3).
McMurry, John, Amides, Organic Chemistry, 1984, 794.
Medical Review, Application No. 21-275, Center for Drug Evaluation and Research, 2001.
Medline, Bimatoprost (Ophthalmic), Bimatoprost, Jul. 24, 2001, 4 pages, Medlineplus. Health Information, Online.

(56) References Cited

OTHER PUBLICATIONS

Michelet, Jean-Francois et al, Activation of Cytoprotective Prostaglandin Synthase-1 by Minoxidil as a Possible Explanation for Its Hair Growth-Stimulating Effect, J. Invest. Dermatol., 1997, 205-209, 108.
Mihele, Densia et al, Cercetarea Actiunii Hepatoprotectoare A Unor Prostaglandine De Sinteza, Farmacia, 1999, 43-58, 67(5).
Millikan, Larry, Treatment of Alopecia, The Journal of Clinical Pharmacology, 1987, 715, 27(8).
Millikan, Larry, Treatment of Male Pattern Baldness, Drug Therapy, 1989, 62-73.
Mishima, Hiromu, A Comparison of Latanoprost and Timolol in Primary Open-Angle Glaucoma and Ocular Hypertension, Arch. Opthalmol., 1996, 929-932, 114.
Miyamoto, Terumasa et al, A Comparison in the Efficacy and Safety Between Ramatroban (BAY u 3405) and Ozagrel-HCl for Bronchial Asthma—A Phase III, Multi-Center, Randomized, Double-Blind, Group Comparative Study, 1997, 599-639.
Mori, S. et al, Effects of Prostaglandin E2 on Production of New Cancellous Bone in the Axial Skeleton of Ovariectomized Rats, Bone, 1990, 103-113, 11.
Morris, Carrie et al, The Role of Bimatoprost Eyelash Gel in Chemotherapy-Induced Madarosis: An Analysis of Efficacy and Safety, Int. J. Trichology, 2011, 84-91, 3(2).
Moses, Robert, Adler's Physiology of the Eye, 1970, 1-18, 5th Ed.
Murakami, T. et al, Effect of Isocarbacyclin Methyl Ester Incorporated in Lipid Microspheres on Experimental Models of Peripheral Obstructive Disease, Drug Res., 1995, 991-994, 45(9).
Narumiya, Shun et al, Roles of Prostanoids in Health and Disease; Lessons From Receptor-Knockout Mice, Common Disease: Genetic and Pathogenetic Aspects of Multifactorial Diseases, 1999, 261-269.
Neau, Steven, Pharmaceutical Salts, Water-Insoluble Drug Formulation, 2008, 417-435.
Negishi, Manabu et al, Molecular Mechanisms of Diverse Actions of Prostanoid Receptors, Biochimica et Biophysica Acta, 1995, 109-120, 1259.
New Drugs for Glaucoma, FDA Consumer Magazine, May-Jun. 2001.
Norrdin, R.W. et al, The Role of Prostaglandins in Bone in Vivo, Prostaglandins Leukotrienes and Essential Fatty Acids, 1990, 139-149, 41.
Ochoa, Blanca, Instilled Bimatoprost Ophthalmic Solution in Patients with Eyelash Alopecia Areata, Letters, Sep. 1, 2009, 530-532, 61(3), J. Am. Acad. Dermatol.
Olsen, Elise et al, Transdermal Viprostol in the Treatment of Male Pattern Baldness, J. Am. Acad. Dermatol., 1990, 470-472, 23.
Orlicky, D.J., Negative Regulatory Activity of a Prostaglandin F2α Receptor Associated Protein (FPRP), Prostaglandins, Leukotrienes and Essential Fatty Acids, 1996, 247-259, 54(4).
Ortonne, Jean-Paul et al, Hair Melanin's Hair Color: Ultrastructural and Biochemical Aspects, Journal of the Society for Investigative Dermatology, 1993, 82S-89S.
Paragraph IV Letter, Jul. 26, 2010.
Pfeiffer, N, New Developments in Glaucoma Drug Therapy, Ophthalmologist, 1992, W1-W13, 89.
Pharmaprojects No. 6321, 2006, 1 page.
Phase 3 Lumigan—AGN 192024—Data Presented at American Academy of Ophthalmology, Allergan Press Release, Mar. 1, 2000.
Physicians' Desk Reference, 56th ed., pp. 212-13, 543, 553-54, 2864-65 (2002).
Poyer, J.F. et al, Prostaglandin F2α Effects on Isolated Rhesus Monkey Ciliary Muscle, Invest. Ophthalmol. Vis. Sci., Nov. 1995, 2461-2465, 36(12).
Preparation of '404 Patent Documents for European Patent Office; Defendant Athena Cosmetics, Inc., Supplemental Invalidity Contentions Pursuant to Patent Local Rule 3-3, 2009.
Preparation of '404 Patent Documents for European Patent Office; Defendant Peter Thomas Roth Labs LLC and Peter Thomas Roth, Inc.'s Invalidity Contentions Pursuant to Patent Local Rule 3-3, 2009.
Preparation of '404 Patent Documents for European Patent Office; Defendants Metrics LLC, Product Innovations LLC; Stella International LLC; and Nutra-Luxe, M.D. LLC's; Local Patent Rule 3-3 Preliminary Invalidity Contentions, 2009.
Preparation of '404 Patent Documents for European Patent Office; Invalidity Contentions Pursuant to Patent Local Rule 3-3, 2008.
Pucci, Neri et al, Long Eyelashes in a Case Series of 93 Children With Vernal Keratoconjunctivitis, Pediatrics, 2005, e86-e91, 115.
Rampton, D.S. et al, Anti-inflammatory Profile in Vitro of Ridogrel, A Putative New Treatment for Inflammatory Bowel Disease, Immunology, Microbiology, and Inflammatory Disorders, 1999, G3477.
Resul, B et al, Phenyl-substituted Prostaglandins: Potent and Selective Antiglaucoma Agents, J. Med. Chem., Jan. 22, 1993, 243-248, 36(2).
Reynolds, A, Darkening of Eyelashes in a Patient Treated With Latanoprost, Eye, 1998, 741-743, 12.
Richer, Marie-Claire et al, Living in It, Living With It, and Moving On: Dimensions of Meaning During Chemotherapy, 2002, 113-119, 29(1).
Rigaudy, J. et al, Nomenclature of Organic Chemistry Sections A, B. C, D, E, F, and H, InCL Union of Pure & Applied Chemistry, Organic Chemistry Div., Comm'n on Nomenclature of Organic Chemistry, 1979, 255-256.
Roenigk, Henry, New Topical Agents for Hair Growth, Clinics in Dermatology, 1988, 119-121, 6(4).
Romano, Maria Rosaria et al, Evidence for the Involvement of Cannabinoid DB1 Receptors in the BimatoprostInduced Contractions on the Human Isolated Ciliary Muscle, Investigative Ophthalmology & Visual Science, Aug. 2007, 3677-3382, 48(8).
Roof, S.L. et al, mRNA Expression of Prostaglandin Receptors EP1, EP2, EP3 and EP4 in Human Osteoblast-Like Cells and 23 Human Tissues, 18 Annual Meeting of the American Society for Bone and Mineral Research, 1996, S337.
Roseborough, Ingrid et al, Lack of Efficacy of Topical Latanoprost and Bimatoprost Ophthalmic Solutions in Promoting Eyelash Growth in Patients with Alopecia Areata, J Am Acad Dermtol, Apr. 2009, 705-706, 60(4).
Ruel, Rejean et al, New Class of Biphenylene Dibenzazocinones as Potent Ligands for the Human EP1 Prostanoid Receptor, Bioorganic & Medicinal Chemistry Letters, 1999, 2699-2704, 9.
Sakuma, Yoko et al, Crucial Involvement of the EP4 Subtype of Prostaglandin E Receptor in Osteoclast Formation by Proinflammatory Cytokines and Lipopolysacharide, Journal of Bone and Mineral Research, 2000, 218-227, 15(2).
Sauk, John et al, Influence of Prostaglandins E1, E2, and Arachidonate on Melanosomes in Melanocytes and Keratinocytes of Anagen Hair Bulbs in Vitro, The Journal of Investigative Dermatology, 1975, 332-337, 64.
Shaikh, M.Y. et al, Hypertrichosis of the Eyelashes From Prostaglandin Analog Use: a Blessing or a Bother to the Patient?, Journal of Ocular Pharmacology and Therapeutics, 2006, 76-77, 22(1).
Sharif, N.A. et al, [3H]AL-5848 ([3H]9β-(+)-Fluprostenol). Carboxylic Acid of Travoprost (AL-6221), a Novel FP Prostaglandin o Study the Pharmacology and Autoradiographic Localization of the FP Receptor, J. Pharm. Pharmacol., 1999, 685-694, 51.
Sharif, N.A. et al, Cat Iris Sphincter Smooth-Muscle Contraction: Comparison of FP-Class Prostaglandin Analog Agonist Activities, J. Ocul. Pharmacol. Ther, Apr. 2008, 152-163, 24(2).
Sharif, N.A. et al, Human Ciliary Muscle Cell Responses to FP-class Prostaglandin Analogs: Phosphoinositide Hydrolysis, Intracellular Ca2+ Mobilization and MAP Kinase Activation, J. Ocul. Pharmacol Ther., 2003, 437-455, 19.
Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.
Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).

(56) References Cited

OTHER PUBLICATIONS

Sharif, N.A. et al, Update and Commentary on the Pro-Drug Bimatoprost and a Putative Prostamide Receptor, Expert Rev. Ophthalmol., 2009, 477-489, 4(5).
Sharif, Najam, Bimatoprost and Its Free Acid Are Prostaglandin FP Receptor Agonists, European Journal of Pharmacology, 2001, 211-213, 432.
Sherwood, Mark et al, Six-Month Comparison of Bimatoprost Once-Daily and Twice-Daily with Timolol Twice-Daily in Patients with Elevated Intraocular Pressure, Survey of Ophthalmology, 2001, S361-S368, 45(4).
Shih, Mei-Shu et al, PGE2 Induces Regional Remodeling Changes in Haversian Envelope: a Histomorphometric Study of Fractured Ribs in Beagles, Bone and Mineral, 1986, 227-264, 1.
Shimazaki, Atsushi et al, Effects of the New Ethacrynic Acid Derivative SA9000 on Intraocular Pressure in Cats and Monkeys, Biol. Pharm. Bull., 2004, 1019-1024, 27(7).
Shimazaki, Atsushi et al, New Ethacrynic Acid Derivatives as Potent Cytoskeletal Modulators in Trabecular Meshwork Cells, Bio. Pharm. Bull., 2004, 846-850, 27(6).
Sjoquist, Birgitta et al, Ocular and Systemic Pharmacokinetics of Latanoprost in Humans, Surv. Ophthalmol., Aug. 2002, S6-S12, 47(Suppl 1).
Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.
Sorbera, L.A. et al, Travoprost, Drugs of the Future, 2000, 41-45, 25(1).
Souillac, Pierre et al, Characterization of Delivery Systems, Differential Scanning Calorimetry, 1999, 212-227, 49.
Spada, C.S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).
Sredni, Benjamin et al, The Protective Role of the Immunomodulator AS101 Against Chemotherapy-Induced Alopecia Studies on Human and Animal Models, Int. J. Cancer, 1996, 97-103, 65.
Stahl, Heinrich et al, Chapter 12: Monographs on Acids and Bases, Handbook of Pharmaceutical Salts, 2008, 265-327.
Stamer, W.D. et al, Cellular Basis for Bimatoprost Effects on Human Conventional Outflow, Invest. Ophthalmol. Vis. Sci., 1012010, 5176-5181, 51(10).
Stjernschantz, Johan et al, From PGF2α-isopropyl Ester to Latanoprost: A Review of the Development of Xalatan: The Proctor Lecture, Invest. Ophthalmol. Vis. Sci., May 2001, 1134-1145, 42(6).
Stjernschantz, Johan et al, Phenyl Substituted Prostaglandin Analogs for Glaucoma Treatment, Phenyl Substituted Prostaglandin Analogs for Glaucoma Treatment, 1992, 691-704, 17(8).
Stjernschantz, Johan et al, Studies on Ocular Inflammation and Development of a Prostaglandin Analogue for Glaucoma Treatment, Exp. Eye Res., Apr. 2004, 759-766, 78(4).
Supplement A (Lumigan®), Physician's Desk Reference 2001, Mar. 2001.
Swarbrick, James et al, Salt Forms of Drugs and Absorption, Encyclopedia of Pharmaceutical Technology, 1988, 453-499, 13.
Terada, Nobuhisa et al, Effect of a Thromboxane A2 Receptor Antagonist Ramatroban (BAY u 3405), on Inflammatory Cells, Chemical Mediators and Non-Specific Nasal Hyperreactivity After Allergen Challenge in Patients with Perennial Allergic Rhinitis, Allergoloy International, 1998, 59-67, 47.
The Newsletter of Glaucoma Foundation, 2000, 11 pages, 11(2).
Tomita, Yasushi et al, Melanocyte-Stimulating Properties of Arachidonic Acid Metabolites: Possible Role in Postinflammatory Pigmentation, Pigment Cell Research, 1992, 357-361, 5.
Tosti, Antonella et al, Drug-Induced Hair Loss and Hair Growth: Incidence, Management and Avoidance, Drug Safety, 1994, 310-317, 10(4).
Tosti, Antonella et al, Hypertrichosis of the Eyelashes Caused by Bimatoprost, J Am Acad Dermatol, Nov. 2004, S149-S150, 51(5).

Travatan (travoprost ophthalmic solution) 0.004% Product Insert, NDA 21-257, Mar. 16, 2001, 7 Pages.
Trueb, Ralph, Chemotherapy-Induced Alopecia, Semin Cutan Med Surg, 2009, 11-14, 28.
U.S. Appl. No. 11/805,122, Resp. to Office Action dated Jan. 21, 2009.
Ueda, Ken et al, Cortical Hyperostosis Following Long-Term Administration of Prostaglandin E1 in Infants with Cyanotic Congenital Heart Disease, Journal of Pediatrics, 1980, 834-836, 97(5).
Ulrich, Jens et al, Skin Toxicity of Anti-Cancer Therapy, J Dtsch Dermatol Ges., 2008, 959-975, 6.
Van Alphen, G.W.H.M. et al, The effect of Prostaglandins on the Isolated Internal Muscles of the Mammalian Eye, Including Man, Documenta Ophthalmologica, 1977, 397-415, 42(4).
Vandenburg, A.M. et al, A One-Month Dose Response Study of AGN 192024, A Novel Antiglaucoma Agent, in Patients with Elevated Intraocular Pressure, Glaucoma Clinical Pharmacology IV Poster Presentation, 1999, S830, 40 (4).
Vandenburgh, Amanda, reply to Alan L. Robin, An Accurate Comparison of Bimatoprost's Efficacy and Adverse Effects, Arch Ophthalmol, Jul. 2002, 997-1000, 120.
Vayssairat, Michael, Preventive Effect of an Oral prostacyclin Analog, Beraprost Sodium, on Digital Necrosis in Systemic Sclerosis, J. Rheumatol, 1999, 2173-2178, 26.
Vengerovsky, A.I. et al, Hepatoprotective action of prostaglandins, Experimental and Clinical Pharmacology, 1997, 78-82, 60(5).
Verbeuren, T. et al, The TP-Receptor Antagonist S 18886 Unmasks Vascular Relaxation and Potentiates the Anti-Platelet Action of PGD2, New Antithrombotic Agents, Jun. 11, 1997, 693.
Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).
Villumsen, J. et al, Prostaglandin F2α-isopropylester Eye Drops: Effect on Intraocular Pressure in Open-Angle Glaucoma, Br. J. Ophthalmol., 1989, 975-979, 73.
Vincent, J.E. et al, Letter to the Editor Prostaglandin Synthesis and Selenium Deficiency a Hypothesis, Prostaglandins, 1974, 339-340, 8(4).
Vippagunta, Sudha et al, Crystalline Solids, Advanced Drug Delivery Reviews, 2001, 3-26, 48.
Voss, N.G. et al, Induction of Anagen Hair Growth in Telogen Mouse Skin by Topical Latanoprost Application, Glaucoma Pharmacology, Cellular, Mechanism II, Mar. 15, 1999, S676, 40(4).
Waddell, K.A. et al, Combined Capillary Column Gas Chromatography Negative Ion Chemical Ionization Mass Spectrometry of Prostanoids, Biomedical Mass Spectrometry, 1983, 83-88, 10(2).
Wand, Martin, Latanoprost and Hyperpigmentation of Eyelashes, Arch Ophthalmology, Sep. 1997, 1206-1208, 115.
Wang, Yili et al, Design and Synthesis of 13,14-Dihydro Prostaglandin F1α Analogues as Potent and Selective Ligands for the Human FP Receptor, J. Med. Chem., 2000, 945-952, 43.
Watson, Peter et al, A Six-month, Randomized, Double-masked Study Comparing Latanoprost with Timolol in Open-Angle Glaucoma and Ocular Hypertension, Ophthalmology, 1996, 126-137, 103.
Whitcup, Clinical Study Report, A Multi-Center, Investigator-Marked, Randomized, Parallel Study of the Safety and Efficacy of AGN 192024 0.03% Ophthalmic Solution Compared with Latanoprost 0.005% Ophthalmic Solution Administered Once-Daily in Subjects with Glaucoma or Ocular Hypertension, Study No. 192024-010-01, Phase 3b, 1999, 1, Allergan.
White, J.H. et al, Heterodimerization is Required for the Formation of a Functional GABA(B) Receptor, Nature, Dec. 17, 1998, 679-682, 396(6712).
Whitson, Jess, Travoprost—a New Prostaglandin Analogue for the Treatment of Glaucoma, Expert Opin. Pharmacother, 2002, 965-977, 3 (7).
Williams, Jane et al, A Narrative Study of Chemotherapy-Induced Alopecia, 1999, 1463-1468, 26(9).
Willis, Anthony, Prostaglandins and Related Lipids, vol. I, Chemical and Biochemical Aspects, CRC Handbook of Eicosanoids, 1987, 80-97, 1.

(56) References Cited

OTHER PUBLICATIONS

Wilson, S.J. et al, Dimerization of the Human Receptors for Prostacyclin and Thromboxane Facilitates Thromboxane Receptor-Mediated CAMP Generation, J. Biol. Chem., Dec. 17, 2004, 53036-53047, 279(51).
Woodward, David et al, Bimatoprost Effects on Aqueous Humor Dynamics in Monkeys, J. Ophthalmol., 2010, 1-5, vol. 2010.
Woodward, David et al, Bimatoprost: a Novel Antiglaucoma Agent, Cardiovascular Drug Reviews, 2004, 103-120, 22(2).
Woodward, David et al, Emerging Evidence for Additional Prostanoid Receptor Subtypes, Current Topics in Pharmacology, 1998, 153-162, 4.
Woodward, David et al, Identification of an Antagonist That Selectively Blocks the Activity of Prostamides (Prostaglandin-Ethanolamides) in the Feline Iris, British Journal of Pharmacology, 2007, 342-352, 150.
Woodward, David et al, Molecular Characterization and Ocular Hypotensive Properties of the Prostanoid EP2 Receptor, Journal of Ocular Pharmacology, 1995, 447-454, 11(3).
Woodward, David et al, Prostaglandin F2α (PGF2α) 1-Ethanolamide: A Unique Local Hormone Biosynthesized From Anandamide, 11th Intl Conf. Advances Prostaglandin & Leukotriene Res.: Basic Sci. & New Clinical Applications—Abstract Book 27, 2000, 1 page.
Woodward, David et al, Replacement of Carboxylic Acid Group of Prostaglandin F2α with a Hydroxyl or Methoxy Substituent Provides Biologically Unique Compounds, British Journal of Pharmacology, Aug. 2000, 1933-1943, 130(8).
Woodward, David et al, Studies on the Ocular Effects of Pharmalogically Novel Agent Prostaglandin F2α 1-OCH3 (AGN 191129), Eicosanoids, 1998, R719.
Woodward, David et al, The Pharmacology of Bimatoprost (LumiganTM), Surv Ophthalmol, 2001, S337-S345, Suppl 4.
Woodward, David, Pharmacological Characterization of a Novel Antiglaucoma Agent, Bimatoprost (AGN 192024), J. Pharmacol. Exp. Ther., Jan. 24, 2003, 772-785, 305 (2).
XALATAN (Latanoprost Ophthalmic Solution) 0.005% Product Insert, 2001, 4 Pages.
Xalatan ® Eye Drops, Retrieval Date : Oct. 2, 2010, 3 pages, http://home.intekom.com/pharm/pharmaca/xalatan.html.
Yamaji, K. et al, Prostaglandins E1 and E2, but not F2α or Latanoprost, Inhibit Monkey Ciliary Muscle Contraction, Curr. Eye Res., Aug. 2005, 661-665, 30(8).
Yoelin, Steve et al, Safety, Effectiveness, and Subjective Experience with Topical Bimatoprost 0.03% for Eyelash Growth, Dermatol. Surg., 2010, 638-649, 36.
Zeigler, Tania, Old Drug New Use: New Research Shows Common Cholesterol-Lowering Drug Reduces Multiple Sclerosis Symptoms in Mice, National Institute of Neurological Disorders and Stroke, Jan. 6, 2003, 2 Pages.
Zimbric, M.L. et al, Effects of Latanoprost of Hair Growth in the Bald Scalp of Stumptailed Macaques, Glaucoma Pharmacology, Cellular Mechanism II, 1999, 3569-B427—Abstract, vol. 40, No. 4.
United States Court of Appeals for the Federal Circuit, *Allergan, Inc., and Duke University v. Apotex Inc., Apotex Corp., Sandoz, Inc., and Hi-Tech Pharmacal Co., Inc.*, 2014, 41 Pages.
Allen by, AC. et al, Mechanism of Action of Acclerants on Skin Penetration, Br. J. Derm, 1969,47-55, 81{Supp. 4).
Bird, Katie, Nano Carriers Enhance Skin Penetration and Antioxidant Effect of CoQ10, Cosmetics design-asia.com, Apr. 8, 2010,1 Page, nla, William Reed Business Media SAS.
Colombe, Laurent et al, Prostaglandin metabolism in human hair follicle, Experimental Dermatology, May 16, 2007, 762-769, 16, US.
Emu Oil Hairloss and Frontal Regrowth, 2010, 4 Pages, www.hairloss-research.org/blog/?p=73.
Ezure, T et al, Involvement of Sonic Hedgehog in Cyclosporine A Induced Initiation of Hair Growth, Journal of Dermatological Science, 2007, 168-170,47.
Fang, Jia-You et al, In Vitro and in Vivo Evaluations of the Efficacy and Safety of Skin Permeation Enhancers Using Flurbiprofen as a Model Drug, International Journal of Pharmaceutics, 2003, 153-166,255.
Green Tea Consumption Grows Hair, Protects Against UV Radiation in Animal Models, 2010, 4 Pages, www.hairloss-research.org/blog/?p=4.
Grice, Jeffrey et al, Relative Uptake of Minoxidil into Appendages and Stratum Corneum and Permeation Through Human Skin in Vitro, Journal of Pharmaceutical Sciences, Feb. 2010, 712-718, 99(2).
Kreilgmrd, Mads, Influence of Microemulsions on Cutaneous Drug Delivery, Advanced Drug Delivery Reviews, 2002, S77-S98, 54 Suppl. 1.
Muller-Rover, Sven et al, A Comprehensive Guide for the Accurate Classification of Murine Hair Follicles in Distinct Hair Cycle Stages, J. Invest Dermatol, 2001, 3-15, 117.
Mura, Simona et al, Penetration Enhancer-Containing Vesicles (PEVs) as Carriers for Cutaneous Delivery of Minoxidil, International Journal of Pharmaceutics, 2009, 72-79, 380.
Saeki, Hideshisa et al, Guidelines for Management of Atopic Dermatitis, Journal of Dermatology, 2009, 563-577, 36.
Scheider, Marlon et al, The Hair Follicle as a Dynamic Miniorgan, Current Biology, 2009, R132-R142, 19.
Titus, Reuben, Aloe Vera—The Magical Plant Amongst Us, 2009, 12 Pages, http://www.scribd.com/doc/19139862/Aloe-VeraMiracle-Plant.
Tobin, Desmond, Aging of the Hair Follicle Pigmentation System, Int. J. Trichology, Jul.-Dec. 2009,83-93,1(2).
Topical Emu Oil and Coconut Oil for Hair Loss—A Potent Combination, 2010, 3 Pages, www.hairloss-research.org/blogl?p=15.
Uno, Hideo et al, Effect of Latanoprost on Hair Growth in the Bald Scalp of the Stump-Tailed Macacque: A Pilot Study, Acta Derm Venereol, 2002, 7-12, 82.
Verma, Do et al, Treatment of Alopecia Areata in the DEBR Model Using Cyclosporin A Lipid Vesicles, Eur. J. Dermatol, 2004, 332-338, 14.
Maurer, M et al,Hair Growth Modulation by Topical Immunophilin Ligands, Amer. J. Path. 1997, 150: 1433-1441 (4).
Transmittal of the International Search Report & Written Opinion mailed on Feb. 20, 2013 for PCT/US2013/021023 filed on Jan. 10, 2013 in the name of Allergan, Inc.

Fig. 1: Example of the Effect of Bim 0.03% on Eyelash Growth Compared to Vehicle – Post-chemotherapy population

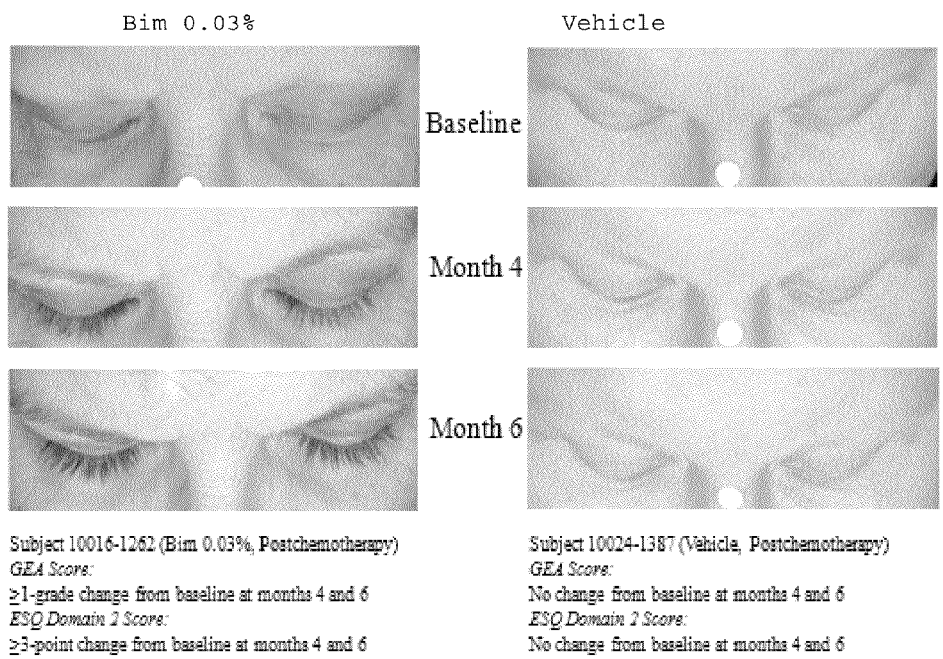

Subject 10016-1262 (Bim 0.03%, Postchemotherapy)
*GEA Score:*
≥1-grade change from baseline at months 4 and 6
*ESQ Domain 2 Score:*
≥3-point change from baseline at months 4 and 6

Subject 10024-1387 (Vehicle, Postchemotherapy)
*GEA Score:*
No change from baseline at months 4 and 6
*ESQ Domain 2 Score:*
No change from baseline at months 4 and 6

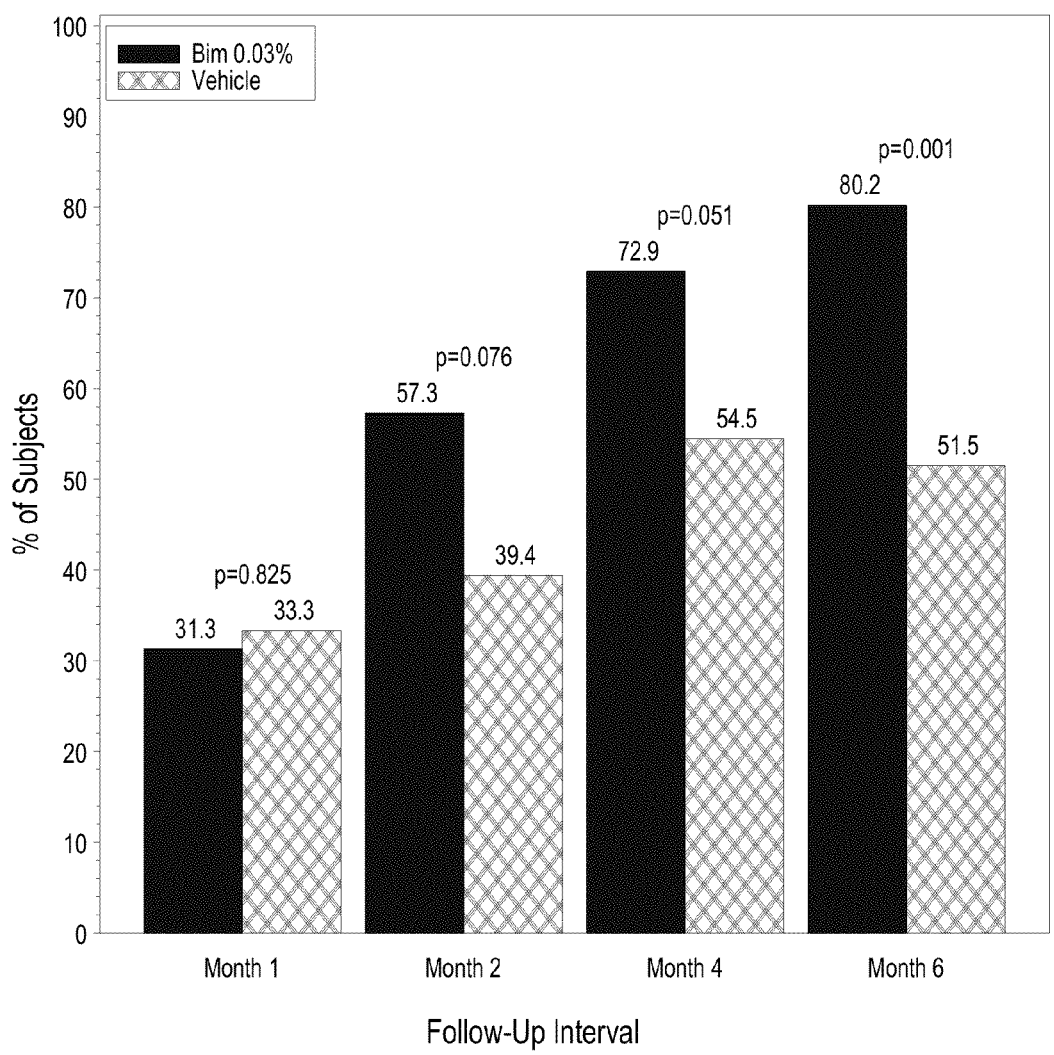
Fig. 2 Percentage of Subjects With at Least a 1-Grade Improvement in GEA Score – Post-chemotherapy

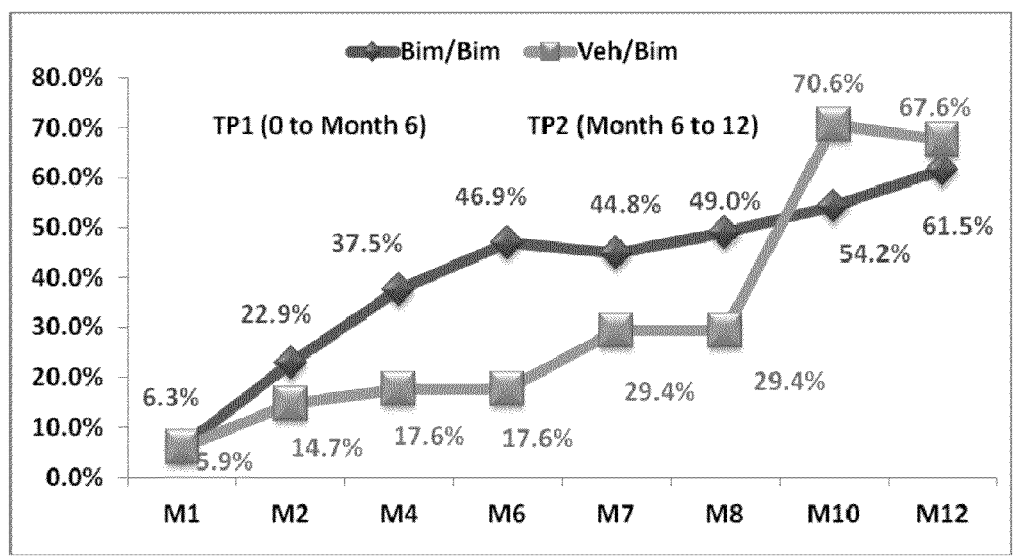
Fig. 3. Treatment Responders (%) Based on Primary Composite Variable by Month: Post-chemotherapy (Intent-to-treat Population)

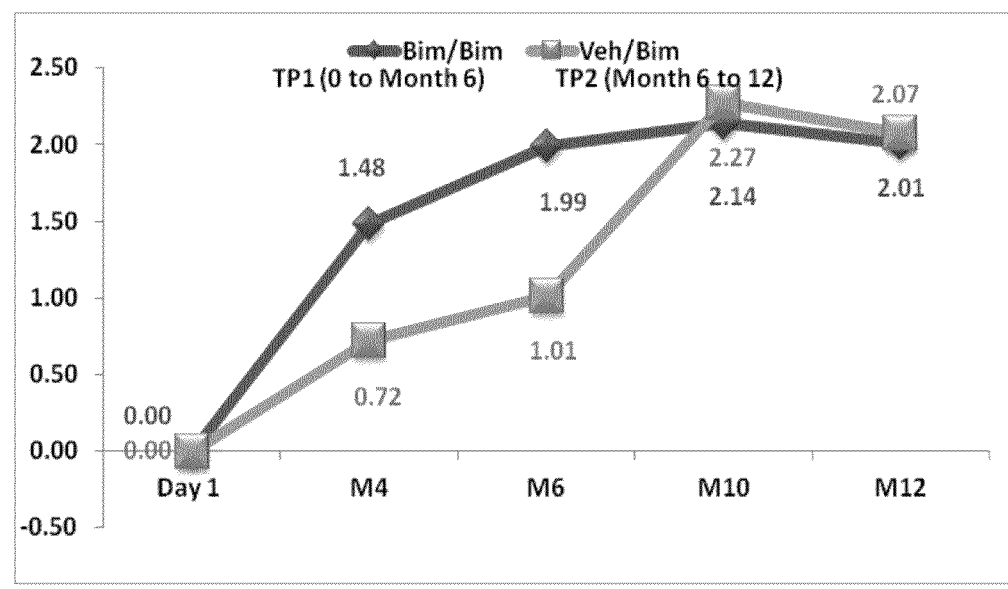
Fig. 4. Mean Change From Baseline in Eyelash Length (mm) by Month: Post-chemotherapy

TOPICAL TREATMENT FOR CHEMOTHERAPY INDUCED EYELASH LOSS OR HYPOTRICHOSIS USING PROSTAMIDE F2 ALPHA AGONISTS

CROSS REFERENCE TO RELATED APPLICATIONS

This application is a continuation of U.S. patent application Ser. No. 13/738,732, filed Jan. 10, 2013, which claims priority to U.S. Provisional Application No. 61/611,920, filed Mar. 16, 2012, and U.S. Provisional Application No. 61/584,877, filed Jan. 10, 2012. This application is also a continuation-in-part of U.S. patent application Ser. No. 13/937,512, filed Jul. 9, 2013, which is a continuation of U.S. patent application Ser. No. 13/441,783, filed Apr. 6, 2012, now U.S. Pat. No. 8,632,760, issued Jan. 21, 2014, which is a continuation of U.S. patent application Ser. No. 13/356,284, filed Jan. 23, 2012, now U.S. Pat. No. 8,263,054, issued Sep. 11, 2012, which is a continuation of U.S. patent application Ser. No. 12/425,933, filed Apr. 17, 2009, now U.S. Pat. No. 8,298,518, issued Oct. 30, 2012, which is a continuation of U.S. patent application Ser. No. 11/943,714, filed Nov. 21, 2007, now U.S. Pat. No. 8,038,988, issued Oct. 18, 2011, which is a continuation of U.S. patent application Ser. No. 11/805,122, filed May 22, 2007, now U.S. Pat. No. 8,101,161, issued Jan. 24, 2012, which is a continuation of U.S. patent application Ser. No. 10/345,788, which was filed on Jan. 15, 2003, now U.S. Pat. No. 7,351,404, issued Apr. 1, 2008, which claims the benefit of U.S. Provisional Application No. 60/354,425, filed on Feb. 4, 2002, all of which are hereby incorporated by reference in their entireties.

FIELD OF THE INVENTION

The present invention is directed to methods and treatments of post-chemotherapeutic hypotrichosis. More specifically, the present invention is directed to the use of compositions comprising bimatoprost for the treatment of post-chemotherapeutic hypotrichosis.

BACKGROUND OF THE INVENTION

Eyelashes, in addition to their contribution to appearance, serve a functional role by protecting sensitive eye structures against foreign particles entering the eye. The nerve plexus that surrounds hair follicles has a very low threshold for excitation (Moses, 1970); as a result, dust or other particles that may come into contact with the eyelash hair fiber are sufficient stimuli to produce a blink reflex, thereby protecting the eye. In terms of the aesthetic function of eyelashes, eyelash prominence has been observed to be related to the attractiveness of individuals, with long, thick eyelashes considered to be a desirable physical attribute with a positive psychological effect (Shaikh and Bodla, 2006).

Inadequate or not having enough eyelashes is known as hypotrichosis of the eyelashes. Etiologies of hypotrichosis of the eyelashes in an adult population include idiopathic hypotrichosis, alopecia-inducing medication (e.g., chemotherapeutic agents) and underlying cutaneous or systemic diseases/conditions (eg, alopecia greata or hypothyroidism).

In healthy adults, eyelash hypotrichosis is often idiopathic and may be related to age. There is an inverse relationship between age and length of eyelashes; younger populations naturally tend to have longer eyelashes, while older populations tend to have shorter eyelashes (Pucci, 2005). For this reason, many otherwise healthy adults experience hypotrichosis as a consequence of aging.

A treatment is available for the natural hypotrichosis condition which may be result of person's genetic makeup or could be age related. Bimatoprost solution 0.03% (LATISSE®) is marketed for the treatment of hypotrichosis of the eyelashes. Bimatoprost is a synthetic prostamide. Topical application of bimatoprost solution can be used in normal healthy adults with inadequate amount of eyelashes or subject who want to further enhance the prominence of their eyelashes (Yoelin, 2010). Treatment with bimatoprost has been demonstrated to increase the percentage of eyelash follicles in anagen, which accounts for its ability to lengthen eyelashes. Bimatoprost-induced stimulation of melanogenesis in melanocytes present in dermal papilla which are responsible for hair shaft pigmentation results in darker eyelashes and, at the same time, appears to increase the size of the dermal papilla and hair bulb, affecting lash thickness and fullness (Cohen, 2010; Fagien, 2010; Law, 2010).

In contrast to the natural eyelash hypotrichosis condition where the hair follicle is normal except it produces shorter and inadequate amount of eyelashes, chemotherapy treatment results in damage to the hair follicle components that make the hair fiber such that after the chemotherapy drug treatment, the natural eyelashes either fall off completely or result in patchy hair loss. Chemotherapeutic agents are well known for their ability to cause hair loss. Other drugs that can cause hair loss to varied degrees include anticoagulants, anti-thyroid drugs, oral contraceptives, lithium, interferons, antihyperlipidemic drugs, and retinoids (Tosti et al, 1994). Chemotherapy-induced hair loss is known to result from the direct toxic insult to rapidly dividing cells of the hair follicle (Trueb, 2009). During the anagen phase of the hair cycle, the epithelial compartment of the follicle undergoes proliferation, with the greatest proliferative activity occurring in the bulb matrix cells as they build up the hair shaft. When cell mitosis abruptly ceases as a result of cytotoxic therapy, the partially keratinized hair shaft weakens and falls out, resulting in anagen dystrophic effluvium (Ulrich et al, 2008). In addition, some chemotherapeutic agents can cause apoptosis (ie, programmed cell death) in the follicular epithelium resulting in premature transitioning from anagen to catagen phases of the hair cycle; this process is known as telogen effluvium (Ulrich et al, 2008). The consequence of these processes is hair shedding, which can begin within 1 to 3 weeks and is often complete within 1 to 2 months after beginning chemotherapy (Trueb, 2009). Hair loss occurs with an estimated incidence of 65% in adult patients receiving chemotherapy (Trueb, 2009). While eyelash loss can be part of the experience of chemotherapy-induced hair loss (Trueb, 2009), there are no reliable data in the published literature that specifically address the incidence of eyelash loss due to chemotherapy. However, the known mechanism by which chemotherapy induces alopecia indicates that any active hair follicle in anagen would be susceptible, including scalp, body, eyebrow, and eyelash hair.

For most cancer treatments, after the chemotherapy regimen is completed, the patient recovers from the treatment side effects relatively quickly, ie, most side effects of chemotherapy resolve within a few weeks of the last treatment; however, hair growth can continue to be depressed for a period of time. It can take several months to a year, or even longer in some subjects, for hair growth to restore to pre-chemotherapy levels. Moreover, when the hair does recover early, it is generally much finer and thinner than the original hair and can take several hair cycles to restore to the pre-chemotherapy levels.

Hair loss is known to be one of the most psychologically upsetting side effects of cancer therapy (Botchkarev, 2003, Lemieux et al, 2008; Hunt, 2005); it has been described by patients as a constant reminder of their illness and is associated with a loss of control, an altered sense of self, and reduced social functioning (Beisecker et al, 1997; Cowley, 2000; Freedman, 1994; Luoma and Hakamies-Blomqvist, 2004; Richer and Ezer, 2002; Williams et al, 1999). The loss not just of scalp hair but body hair can lead to psychosocial problems such as diminished quality of life expressed as anxiety, depression, and low self-esteem (Ulrich et al, 2008).

In the focus group studies, patients stated that the loss of eyelashes and eyebrows was worse than the loss of scalp hair because the latter could be easily concealed by a wig, whereas there was no way to make their eyelashes look "normal". False eyelashes were not a reasonable treatment in the opinion of the respondents because they did not have enough natural eyelashes to help the glue adhere to their eyelid margins. Moreover, such measures can result in severe irritation and skin damage and are therefore not ideal, especially in the post-chemotherapy population. In focus-group studies, many post-chemotherapy patients commented that their eyelashes never fully recovered to their pre-chemotherapy levels. Even though they noticed some re-growth, most complained that their eyelashes were sparse (ie, gaps between lashes), short, and lighter in color.

Currently there are no treatments available for chemotherapy induced eyelash loss. We discovered that treatment with LATISSE (bimatoprost 0.03% solution) restores eyelash growth and prominence quickly compared with the natural course of slower recovery. Thus the protective function of eyelashes is resumed earlier in treated patients as compared to non-treated patients. The post-chemotherapy patients treated with bimatoprost 0.03% solution express a higher overall satisfaction with their eyelashes as compared to patients treated with vehicle. Bimatoprost treatment in post-chemotherapy patients also restored length, thickness/fullness and darkness of eyelashes.

BRIEF SUMMARY OF THE INVENTION

The present invention is directed to the use of bimatoprost for the use in growing eyelashes in post-chemotherapeutic patients. The present invention is also directed to the use of bimatoprost during chemotherapy to prevent the loss of eyelashes during chemotherapeutic treatment. The present invention is also directed to the use of bimatoprost to prevent the loss of eyelashes prior to the start of chemotherapy. The present invention is also directed to the use of bimatoprost before, during and after chemotherapeutic treatment.

The present invention may be applied as 0.03% w/v bimatoprost available in the commercial product called LATISSE® and may be applied in concentrations 0.3% w/v to 0.001% w/v and including concentrations such as 1.0% w/v, 0.9% w/v, 0.8% w/v, 0.7% w/v, 0.6% w/v, 0.5% w/v, 0.4% w/v, 0.3% w/v, 0.2% w/v, 0.1% w/v, 0.09% 0.08% w/v, 0.07% w/v, 0.06% w/v, 0.05% w/v, 0.04% w/v, 0.03% w/v, 0.02% w/v, 0.01% w/v, 0.009% w/v, 0.008% w/v, 0.007% w/v, 0.006% w/v, 0.005% w/v, 0.004% w/v, 0.003% w/v, 0.002% w/v, 0.001% w/v, 0.009% w/v, 0.008% w/v, 0.007% w/v, 0.006% w/v, 0.005% w/v, 0.004% w/v, 0.003% w/v, 0.002% w/v, and 0.001% w/v bimatoprost.

Bimatoprost may be applied as a solution, emulsion, gel, foam, spray, ointment, cream, or other form suitable for administration to the eyelid margin. Bimatoprost may be in the form of a salt, pro-drug, analogs including esters of bimatoprost. The bimatoprost composition, including LATISSE®, may also be applied in conjunction with other therapeutics known to grow hair such as Minoxidil® and Propecia®.

"Treatment", "treat" or "treating" can refer to curing any disease or condition or reducing or alleviating the symptoms of the disease or condition.

"Prevent", "preventing" or "prevention" can refer to stopping any disease, condition or symptoms or reducing symptoms in a clinically significant manner, particularly as compared to patients receiving no treatment at all.

Some embodiments of the present invention include the following paragraphs:

1) A method of growing eyelashes in patients undergoing chemotherapy, the method comprising applying 0.03% w/v bimatoprost to the eyelids before, during and after chemotherapeutic treatment;
2) The method of paragraph 1, wherein the 0.03% bimatoprost is applied at least once a day;
3) The method of paragraphs 1 and 2, wherein the method results in eyelashes which are longer, thicker and darker compared to patients receiving no treatment;
4) The method of paragraphs 1 and 2, wherein the method is applied for at least 6 months after completing chemotherapeutic treatment;
5) The method of paragraph 4, wherein the method is applied for at least 12 months after completing chemotherapeutic treatment;
6) The method of paragraph 3, wherein the number of eyelashes increases in comparison to post-chemotherapeutic patients who received no treatment;
7) The method of paragraph 1, wherein the bimatoprost is added before, during and after post-chemotherapeutic treatment;
8) The method of paragraph 2, wherein the method is applied twice a day;
9) The method of paragraphs 2 and 8, wherein the bimatoprost is applied to the upper and lower eyelid margin of each eye;
10) The method of paragraphs 1-9, wherein the method effectively treats post-chemotherapeutic hypotrichosis;
11) The method of paragraph 1, wherein the eyelids include application to the upper and lower eyelid margin;
12) The method of paragraph 1, further comprising the step of administering one selected from the group consisting of Minoxidil® and Propecia®;
13) The method of claim 1, wherein the method results in lower incidence of conjunctival hyperemia, punctate keratitis, erythema of the eyelid, eye pruritis and skin hyperpigmentation than in patients receiving 0.03% w/v bimatoprost for treatment of idiopathic hypotrichosis;
14) A method of preventing loss of eyelashes in patients undergoing chemotherapy, the method comprising applying 0.03% w/v bimatoprost to the eyelids before, during, or after chemotherapeutic treatment;
15) The method of paragraph 14, wherein the 0.03% bimatoprost is applied at least once a day;
16) The method of paragraphs 14 and 15, wherein the method results in eyelashes which are longer, thicker and darker compared to patients receiving no treatment;
17) The method of paragraphs 14 and 15, wherein the method is applied for at least 6 months after completing chemotherapeutic treatment;
18) The method of paragraph 14, wherein the method is applied for at least 12 months after completing chemotherapeutic treatment;
19) The method of paragraph 13, wherein the number of eyelashes increases in comparison to post-chemotherapeutic patients who received no treatment;

20) The method of paragraph 14, wherein the bimatoprost is added before, during and after post-chemotherapeutic treatment; and, 21) The method of paragraph 14, wherein the method is applied twice a day.

BRIEF DESCRIPTION OF THE DRAWINGS

FIG. 1 shows an Example of the Effect of Bim 0.03% on Eyelash Growth Compared to Vehicle—post-chemotherapy population;

FIG. 2 Percentage of Subjects With at Least a 1-Grade Improvement in GEA Score—Post-chemotherapy;

FIG. 3 Shows treatment Responders (%) Based on Primary Composite Variable by Month: Post-chemotherapy (Intent-to-treat Population);

FIG. 4 Shows Mean Change From Baseline in Eyelash Length (mm) by Month: Post-chemotherapy;

DETAILED DESCRIPTION OF THE INVENTION

Example 1

TABLE I

List of Components and Quantitative Composition

Figure 5:
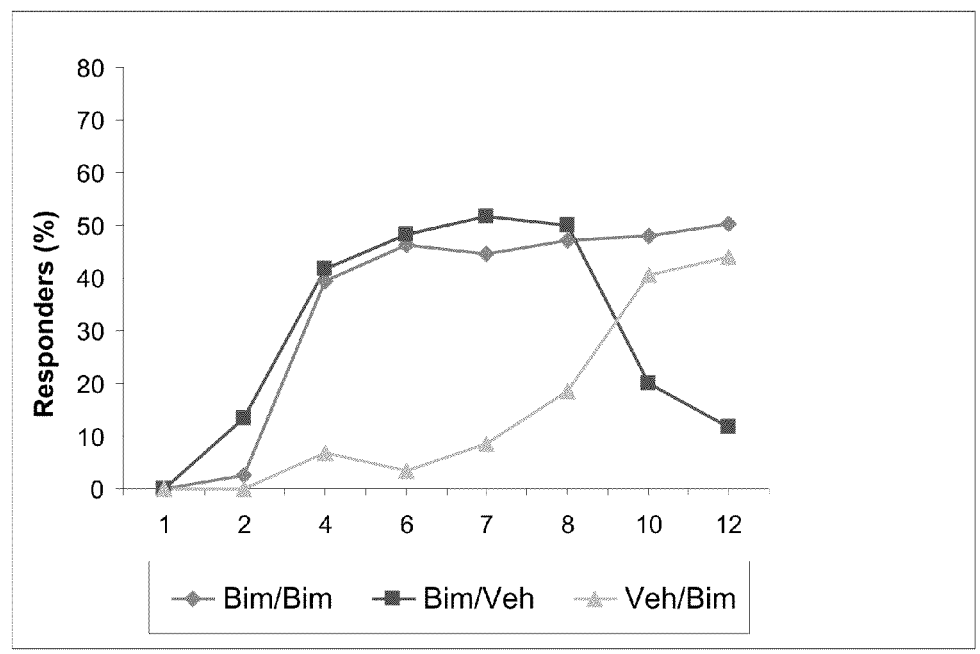
FIG. 5 is a plot of primary composite efficacy for the duration of the trial for subjects with idiopathic hypotrichosis.

| Ingredients | Concentration (% w/v) | Concentration (mg/mL) | Function |
|---|---|---|---|
| Active ingredient | | | |
| Bimatoprost[a] | 0.03 | 0.3 | Active ingredient |
| Other ingredients | | | |
| Benzalkonium chloride[b] | 0.005 | 0.05 | Preservative |
| Sodium phosphate dibasicheptahydrate | 0.268 | 2.68 | Buffering agent |
| Citric acid monohydrate | 0.014 | 0.14 | Buffering agent |
| Sodium chloride | 0.83 | 8.3 | Tonicity agent |
| Hydrochloric acid[c] and/or sodium hydroxide[c] | Adjust to pH 7.2-7.4 | | pH adjuster |
| Purified water | q.s. ad 100% | q.s. ad 1 mL | Vehicle |

Clinical Data:

A clinical study was conducted that demonstrated the clinical benefits of bimatoprost 0.03% solution in treating eyelash loss resulting from chemotherapy treatment.

Study Design and Structure:

This was a 1-year, multicenter, double-masked, randomized, parallel-group study to evaluate the safety and efficacy of bimatoprost solution 0.03% in increasing overall eyelash prominence following dermal application to the upper eyelid margins in normal adults and post-chemotherapy adults exhibiting hypotrichosis of the eyelashes. Subjects enrolled in the study were adult subjects at least 18 years of age, with idiopathic or chemotherapy-induced hypotrichosis (Global Eyelash Assessment [GEA] score of 1 or 2) and had a score of 1 or 2 on each of the 3 items (16, 18, and 19) on the Eyelash Satisfaction Questionnaire (ESQ) Domain 2, which represented psychological impact of eyelash loss.

The full 12-month study consisted of 2 distinct 6-month treatment periods, treatment period 1 (TP1) and treatment period 2 (TP2). Eligible post-chemotherapy subjects were randomly assigned in a 3:1 ratio to receive bimatoprost or vehicle for TP1. In TP2, the subjects were either maintained on or switched to bimatoprost treatment.

A total of 130 subjects with chemotherapy-induced hypotrichosis were randomized. Of these, 96 subjects were randomized to the Bim 0.03% group and 34 subjects to the vehicle group. The overall mean age of the post-chemotherapy subjects was 50.7 years (range 26 to 76 years), and the majority of the population was Caucasian (79.2%). All except 1 of the subjects enrolled were female (99.2%; 129/130). Per inclusion criteria, all enrolled subjects had a baseline GEA score of 1 (71.3%) or 2 (28.7%), with a similar distribution of GEA scores in both treatment groups at baseline. The mean total score±SD of ESQ Domain 2 for was 3.9±1.23. All enrolled subjects had a baseline ESQ score of 1 or 2 for items 16, 18, and 19 that relates to psychological impact of eyelash loss or hypotrichosis condition.

Primary Composite Efficacy Endpoint:

The primary efficacy endpoint was the proportion of treatment responders at month 4 based on a composite endpoint, defined by: a) at least a 1-grade improvement from baseline in the GEA score, and b) at least a 3-point improvement from baseline in the total score for Domain 2 of the ESQ. The GEA is an investigator assessment of eyelash prominence and the ESQ score is patients own perception of their eyelashes.

6 month data:

After 4 months of daily treatment, in the post-chemotherapy subpopulation, the treatment responder rates based on the primary efficacy end point were 37.5% (36/96) in the bimatoprost 0.03% group and 18.2% (6/33) in the vehicle group. Data in the table below shows response rate by visit at month 1, 2, 4, and 6. A continuous improvement in efficacy is observed over the six month time period.

TABLE II

Primary Composite Efficacy Variable: Treatment Responders by Visit

| | Post-chemotherapy population | | |
|---|---|---|---|
| Visit | Bim 0.03% (N = 96) | Vehicle (N = 34) | P-value[b] |
| Month 1 | 6/96 (6.3%) | 2/33 (6.1%) | >0.999[c] |
| Month 2 | 22/96 (22.9%) | 5/33 (15.2%) | 0.344 |

TABLE II-continued

Primary Composite Efficacy Variable: Treatment Responders by Visit

Post-chemotherapy population

| Visit | Bim 0.03% (N = 96) | Vehicle (N = 34) | P-value[b] |
|---|---|---|---|
| Month 4 | 36/96 (37.5%) | 6/33 (18.2%) | 0.041 |
| Month 6 | 45/96 (46.9%) | 6/33 (18.2%) | 0.004 |

The response rate was also determined solely based on the investigator GEA scoring. As shown in FIG. 1, the Bim 0.03% group had a higher responder rate at the month 2, 4, and 6 visits compared with the vehicle group. The difference in responder rate, based on GEA of eyelash prominence, approached statistical significance at month 4 (p=0.051) and was statistically significant at the month 6 visit (p=0.001). The relatively high responder rate in the vehicle group of the post-chemotherapy population compared to the vehicle group of the normal adult population is attributable to the natural re-growth that occurs to some degree upon completion of chemotherapy treatment. FIG. 2 shows the percentage of subjects with at least a 1-grade improvement in GEA Score—Post-chemotherapy.

Efficacy was also assessed using more conservative criteria of 2-grade improvement in GEA. At month 4, the responder rates for the 2-grade increase in the Bim 0.03% group was 36.5% (35/96) compared to vehicle response of 6.1% (2/33) for this 2 grade increase. In addition to the investigator global assessment (GEA) and subjects own assessment (ESQ), the eyelash length, thickness/fullness and darkness were measures using digital image analysis.

The mean change in eyelash length from baseline at month 4 was 1.48 mm in the Bim 0.03% group and 0.72 mm in the vehicle group. By month 6, the mean change in eyelash length from baseline was 1.99 mm for the Bim 0.03% group and 1.01 mm for the vehicle group.

The mean changes in eyelash thickness from baseline at month 4 were 0.67 mm$^2$ in the Bim 0.03% group and −0.05 mm$^2$ in the vehicle group. By month 6, the mean changes in eyelash thickness from baseline were 0.83 mm$^2$ for the Bim 0.03% group and 0.04 mm$^2$ for the vehicle group.

The mean change from baseline in eyelash darkness was greater in the Bim 0.03% than in the vehicle group. At the month 4 and 6 visits, it was −22.48 and −26.46, respectively, in the Bim 0.03% group and −11.25 and −10.19, respectively, in the vehicle group. The greater negative number on this measure reflects the greater intensity or darkness of eyelashes.

Summary of Efficacy Data on Effect of Bimatoprost on Increasing Eyelash Growth in Post-Chemotherapy Population:

For the primary composite efficacy endpoint, the Bim 0.03% group had a statistically significantly higher responder rate than the vehicle group at month 4 (p=0.041). At month 4, the responder rate was 37.5% (36/96) in the Bim 0.03% group and 18.2% (6/33) in the vehicle group. By month 6, the responder rate in the Bim 0.03% group increased to 46.9% (45/96), whereas there was no change in the vehicle group (18.2%, 6/33).

The Bim 0.03% group had a higher percentage of subjects with at least a 1-grade increase from baseline in GEA score compared to the vehicle group at all follow-up visits. The difference between the 2 groups approached statistical significance at month 4 (p=0.051) and was statistically significantly different at the month 6 visit (p=0.001). At the month 4 visit, 72.9% in the Bim 0.03% group and 54.5% in the vehicle group had at least a 1-grade increase from baseline in GEA score. By month 6, the percentage of responders increased to 80.2% in the Bim 0.03% group, whereas in the vehicle group it decreased to 51.5%.

The percentage of subjects with at least a 1-grade increase from baseline in GEA in the Bim 0.03% group of the post-chemotherapy subpopulation (72.9%) was comparable to that of the normal adult subpopulation (74.3%) at month 4. Relative to the vehicle group in the normal adult subpopulation, the vehicle group in the post-chemotherapy subpopulation showed higher GEA response at all visits which is likely related to some degree of natural regrowth in the post-chemotherapy subpopulation.

Statistically significant improvements from baseline in upper eyelash length, thickness, and darkness were seen in the Bim 0.03% group compared to the vehicle group at month 4 and month 6.

At month 4, 36.5% of subjects in the Bim 0.03% group of the post-chemotherapy subpopulation had at least a 2-grade increase from baseline in GEA scores.

Statistically significant improvements in favor of Bim 0.03% group were observed for ESQ Domains 1 and 3 scores at months 4 and 6. For Domain 2, although the improvements were not statistically significantly different between the 2 treatment groups, the Bim 0.03% group had a higher mean change in total score from baseline than the vehicle group (2.8 versus 1.7).

Post-Chemotherapy Population (Safety Summary):

In the post-chemotherapy subpopulation, 57.3% (55/96) of subjects in the Bim 0.03% group and 45.5% (15/33) of subjects in the vehicle group reported at least 1 adverse event over the first 6-month study period. Adverse events that were more common in the Bim 0.03% group (more than 5% of subjects) than in the vehicle group were conjunctival hyperaemia, punctate keratitis and eye pruritus. The majority of adverse events were reported as mild or moderate in severity. The treatment-related adverse events were reported by 27.1% (26/96) and 6.1% (2/33) of subjects in the Bim 0.03% and vehicle groups, respectively. Treatment-related adverse events reported by more than 1 subject in the Bim 0.03% group were conjunctival hyperaemia (12 subjects), punctate keratitis (7 subjects), eyelids pruritus (3 subjects), eye pruritus (3 subjects), skin hyperpigmentation (3 subjects) and eyelid irritation (2 subjects). The 2 treatment-related adverse events reported in the vehicle group were punctate keratitis (1 subject) and eyelids pruritus (1 subject).

None of the treatment-related adverse events were reported as severe, and none of them led to study or treatment discontinuation.

12-Month Data:

For subjects receiving bimatoprost for up to 12 months (Bim/Bim group), the efficacy demonstrated for the composite end point, ie, the proportion of responders increased from month 6 to the month 12 period as shown in the figure below. The responder rate, based on the primary efficacy composite measure, increased from 46.9% at month 6 to 61.5% at month 12. These data indicate continuous improvement seen in the post-chemotherapy population through month 12 of treatment. These data also demonstrate that efficacy is maintained over 12 months of daily exposure, with no indication for development of any resistance to the treatment.

Subjects that received vehicle in the first 6 months of treatment and then switched to bimatoprost in TP2 (Veh/Bim groups), the drug effect was rapidly realized, the responder rate increased from 17.6% (6/34) at month 6 to 67.6% (23/34) at month 12 as shown in FIG. 3.

Eyelash Length:

For the idiopathic hypotrichosis subpopulation treated for up to 12 months with bimatoprost, the mean eyelash length at baseline was 5.69 mm and increased by 1.44 mm at month 6 of treatment, and then remained fairly constant throughout the treatment period. This corresponds to a mean percent increase from baseline of 26.17% at month 6 and 25.86% at month 12, and a median percent increase from baseline of 22.4% at month 6 and 22.63% at month 12. This indicates that eyelash length increase is maintained, with no evidence of development of resistance, from month 6 through 12 of daily treatment.

| | Mean Change ± Standard Deviation (SD) from Baseline in Eyelash Length (mm) | |
|---|---|---|
| | Post-chemotherapy | |
| TP1/TP2/Visit[a] | Bim/Bim (N = 96) | Veh/Bim (N = 34) |
| Baseline | 4.86 ± 1.189 | 4.65 ± 1.413 |
| Month 4 | 1.48 ± 1.391 | 0.72 ± 1.396 |
| Month 6 | 1.99 ± 1.557 | 1.01 ± 1.275 |
| Month 10 | 2.14 ± 1.455 | 2.27 ± 1.439 |
| Month 12 | 2.01 ± 1.504 | 2.07 ± 1.442 |

Bim = bimatoprost 0.03%;
TP1 = treatment period 1 (day 1 to month 6);
TP2 = treatment period 2 (month 6 to 12);
Veh = vehicle For the post-chemotherapy subjects treated for up to 12 months with bimatoprost, the mean eyelash length at baseline was 4.86 mm and increased by 1.99 mm at month 6 of treatment, and then remained fairly constant throughout the treatment period. This corresponds to a mean percent increase from baseline of 48.08% at month 6 and 49.88% at month 12, and a median percent increase from baseline of 37.84% at month 6 and 39.08% at month 12), again indicating that eyelash length increase is maintained, with no evidence of loss of effect upon continuous daily treatment from months 6 through 12 as shown in FIG. 4.

For the post-chemotherapy subjects treated for up to 12 months with bimatoprost, the mean thickness at baseline was 0.39 $mm^2$, which increased by 0.83 $mm^2$ at month 6 of treatment, and then remained fairly constant throughout the treatment period. This corresponds to a mean percent increase from baseline of 428% at month 6 and 478% at month 12, and a median percent increase from baseline of 245% at month 6 and 212% at month 12, again the eyelash thickness increase was maintained, with no evidence of loss of effect upon continuous daily treatment from month 6 through 12.

| | Mean Change ± Standard Deviation (SD) from Baseline in Average Progressive Eyelash Thickness ($mm^2$) | |
|---|---|---|
| | Post-chemotherapy | |
| TP1/TP2/Visit[a] | Bim/Bim (N = 96) | Veh/Bim (N = 34) |
| Baseline | 0.39 ± 0.302 | 0.67 ± 0.995 |
| Month 4 | 0.67 ± 0.514 | −0.05 ± 0.955 |
| Month 6 | 0.83 ± 0.576 | 0.04 ± 1.009 |
| Month 10 | 0.88 ± 0.516 | 0.63 ± 1.042 |
| Month 12 | 0.85 ± 0.575 | 0.58 ± 1.085 |

Bim = bimatoprost 0.03%;
TP1 = treatment period 1 (day 1 to month 6);
TP2 = treatment period 2 (month 6 to 12);
Veh = vehicle
At Least a 2-grade Increase in Global Eyelash Assessment Score A secondary analysis of the GEA component of the primary efficacy variable using a more stringent criterion was the percentage of subjects who experienced at least a 2-grade increase and a 3-grade increase from baseline on the GEA scale. For post-chemotherapy hypotrichosis subjects treated for up to 12 months with bimatoprost, 45.8% of the subjects had at least a 2-grade increase in GEA at month 6, which increased to 57.3% at month 12. This indicates a progressive increase in eyelash prominence from month 6 to 12.

The post-chemotherapy subjects treated with vehicle for the first 6 months and then switched to bimatoprost treatment (Veh/Bim) had only 8.8% (3/34) of the subjects with a 2-grade GEA increase at month 6; this increased to 50% by month 10 (4 months after starting bimatoprost treatment) and to 52.9% by month 12.

Efficacy in the post-chemotherapy hypotrichosis population showed a gradual increase in the number of responders through 12 months of treatment. Though an early peak in the percent responders was observed at month-6 (46.9%) and a minimal change between months-6 and −8, there was a gradual further increase to 54.2% at month-10 and an increase to 61.5% at month-12, indicating a continuous improvement in this population. A similar gradual increase in the percent responders was noted based on at least 1-grade increase in GEA or at least 3-point increase in ESQ Domain-2 from month-6 to the month-12 treatment. The GEA responders increased from 80.2 to 90.6% and the ESQ Domain-2 responders increased from 47.9 to 63.5% between month-6 and −12.

Majority of the common adverse events observed for the entire 12 month period were from the first 6 months of treatment, indicating that continuous treatment does not lead to increased incidence of adverse events. For example, the incidence rate for three of the most common AEs in the post-chemotherapy population, conjunctival hyperaemia, punctate keratitis and eyelids pruritus was 15.6%, 8.3% and 3.1%, respectively, in the first 6 months of treatment vs. only 1.1% (new AE) for each of these three events for months 6-12.

Example 2

This is a long-term safety and efficacy study of bimatoprost ophthalmic solution 0.03% (LATISSE®) bimatoprost carried out in idiopathic and post-chemotherapy hypotrichosis populations. In this study, eyelash loss from chemotherapy was studied.

Study Design:

A one-year, multicenter, randomized, double-masked, vehicle-controlled study. Adult post-chemotherapy and idiopathic eyelash hypotrichosis subjects were enrolled based on their score of 1 or 2 on a four point ordinal Global Eyelash Assessment (GEA) scale, and in addition having a low score on a PRO measure associated with 'psychological impact' of the condition, a domain-2 of the Eyelash Satisfaction Questionnaire (ESQ). The study involved two treatment periods of six months each. In the first treatment period, subjects for both populations were randomized 3:1 for QD bimatoprost: vehicle treatment. In the second 6-month treatment period, all subjects were moved to bimatoprost treatment, except for a group of bimatoprost treated idiopathic hypotrichosis subjects (n=55) who were switched to vehicle to investigate the effect of drug discontinuation. The study included 9 visits over the 12 month treatment period. The primary end point was the proportion of responders within each treatment group based on a composite measure of GEA and ESQ Domain-2 (investigator assessed eyelash prominence and subject's assessment of 'psychological impact' related to eyelashes) at month-4.

Results:

A total of 368 subjects were randomized, 238 idiopathic and 130 post-chemotherapy. The primary efficacy end point was met for both idiopathic and post-chemotherapy populations. A baseline, majority of the post-chemotherapy subjects showed sparse, patchy eyelashes to near complete loss. In both populations, majority of the subjects (>70%) demonstrated increased eyelash prominence (>1 grade GEA improvement) at month-4 following daily bimatoprost treatment. There were no drug related serious adverse events in the study.

In subjects with idiopathic hypotrichosis, 40.2% efficacy (a greater than 1-grade increase in GEA score and at least 3 point improvement in ESA domain score) was achieved at month 4, while only 6.8% of the vehicle treated subjects had a similar increase in GEA after 4 months. Efficacy was maintained over the 12-month trial period. After drug discontinuation, efficacy was maintained for about 2 months, and return to near pre-treatment levels occurred 4 to 6 months after discontinuation. In subjects with chemotherapy-induced hypotrichosis, 37.5% increase in efficacy was achieved at month 4 whereas only 18.2% of the vehicle treated subjects had a similar increase in GEA after 4 months. Efficacy was enhanced over the 12-month trial period.

In subjects with idiopathic hypotrichosis, 74.3% of the bimatoprost treated subjects had an increase in GEA of greater than 1 after 4 months, while only 13.6% of the vehicle treated subjects had a similar increase in GEA after 4 months. In subjects with chemotherapy-induced hypotrichosis, 72.9% of those receiving bimatoprost treatment had an increase of GEA of greater than 1 after 4 months, while 54.5% of the vehicle-treated subjects had a similar increase in GEA after 4 months (due to the natural untreated regrowth of eyelashes after cessation of chemotherapy). Both populations had statistically significant improvements in eyelash length, thickness/fullness, and darkness by bimatoprost compared with vehicle at months 4 and 6 (not shown).

The changes in eyelash length, thickness and darkness are shown in the table below.

| | Eyelash length, thickness, and darkness Percent change from baseline at Month 4 | | | | | |
|---|---|---|---|---|---|---|
| | Idiopathic Hypotrichosis (mean % change) | | | Chemotherapy-Induced Hypotrichosis (median % change) a | | |
| Endpoint | Bim 0.03% | Vehicle | P-value | Bim 0.03% | Vehicle | P-value |
| Length | 22.90% | −4.90% | <.001 | 28.50% | 11.30% | 0.022 |
| Thickness | 95.90% | −7.20% | <.001 | 180.10% | 25.00% | 0.002 |
| Darknessb | −15.70% | 1.40% | <.001 | −14.40% | −5.70% | 0.012 | aMedian values are provided because data from the post-chemotherapy subpopulation did not follow a normal distribution.
bNegative change from baseline indicates darker lashes.

Results for Subjects with Idiopathic Hypotrichosis:

FIG. 5 is a plot of primary composite efficacy for the duration of the trial. Bim/Bim indicates subjects receiving bimatoprost for 12 months. Bim/Veh indicates subjects receiving bimatoprost for 6 months followed by vehicle for 6 months. Veh/Bim indicates subjects receiving vehicle for 6 months followed by bimatoprost for 6 months.

Figure 6:
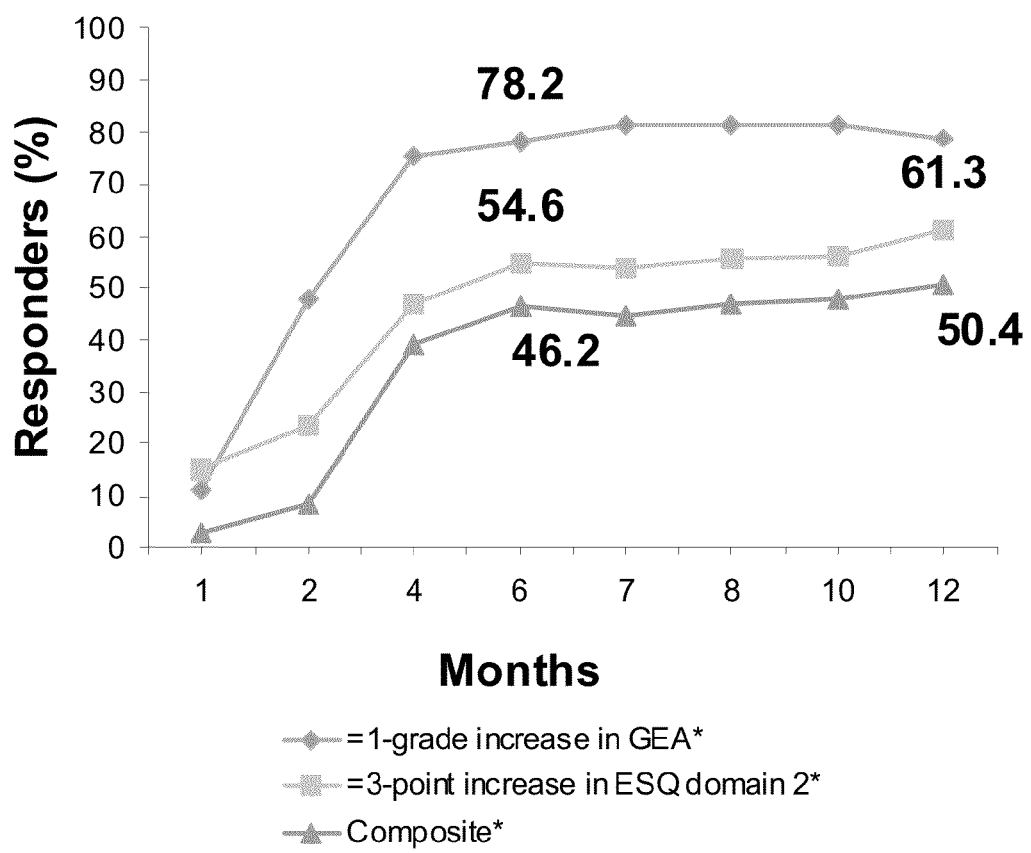
FIG. 6 is a plot of responder rates in bimatoprost-treated subjects by individual components of the primary composite efficacy measure for the duration of the for subjects with idiopathic hypotrichosis.

FIG. 6 is a plot of responder rates in bimatoprost-treated subjects by individual components of the primary composite efficacy measure for the duration of the trial. FIG. 6 shows a GEA response rate of about 75% to about 80% and a maintenance of the effect and/or continuous improvement up to month 12.

Figure 7:
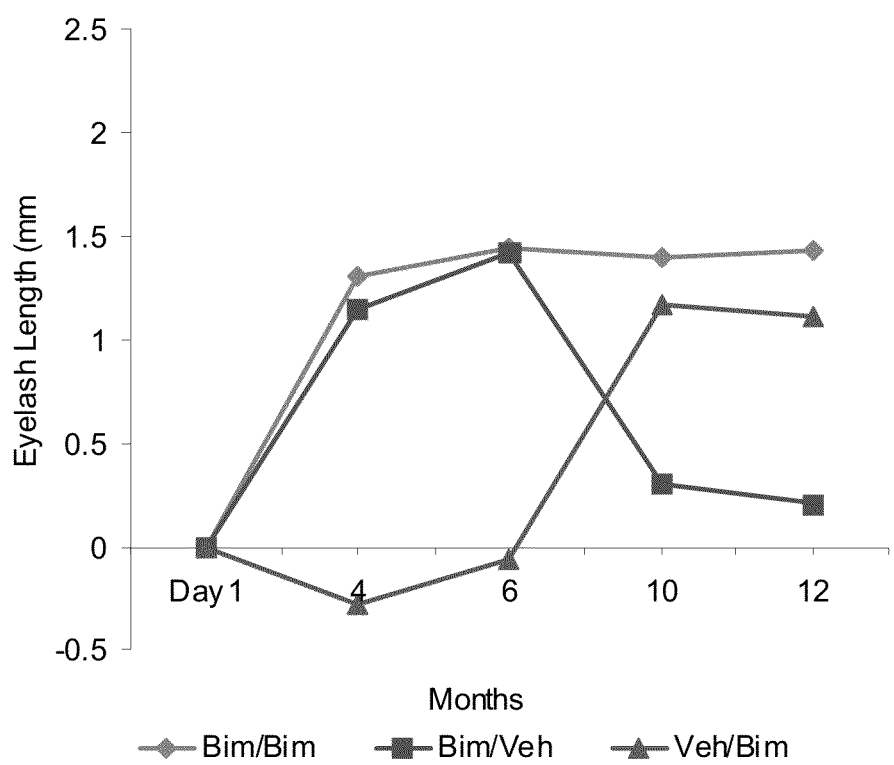
FIG. 7 is a plot of improvement in eyelash length for the duration of the trial for subjects with idiopathic hypotrichosis.

FIG. 7 is a plot of improvement in eyelash length for the duration of the trial. Bim/Bim indicates subjects receiving bimatoprost for 12 months. Bim/Veh indicates subjects receiving bimatoprost for 6 months followed by vehicle for 6 months. Veh/Bim indicates subjects receiving vehicle for 6 months followed by bimatoprost for 6 months.

Figure 8:
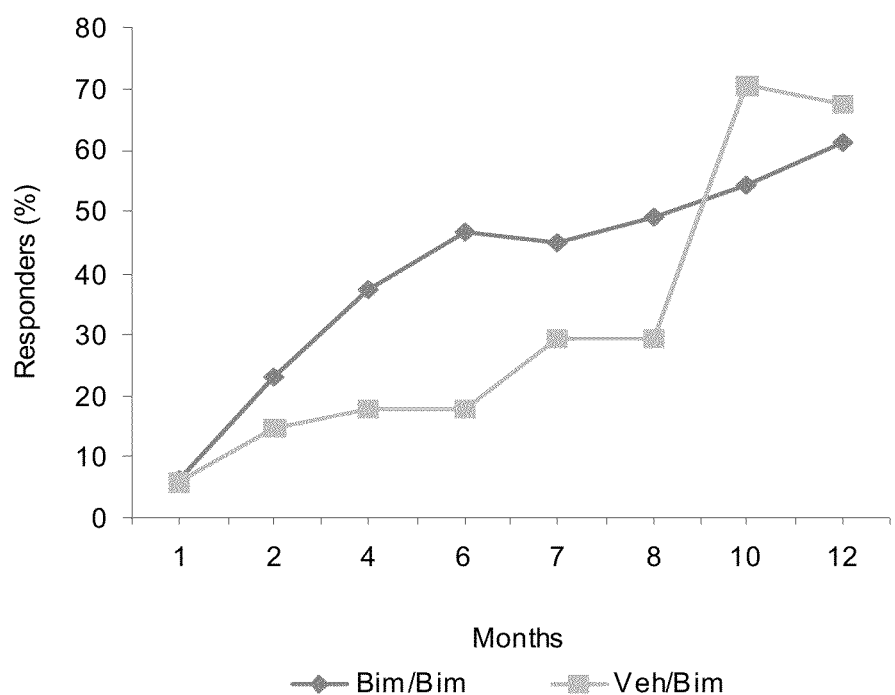
FIG. 8 is a plot of primary composite efficacy for the duration of the trial for subjects with chemotherapy-induced hypotrichosis.

Results for Subjects with Chemotherapy-Induced Hypotrichosis:

FIG. 8 is a plot of primary composite efficacy for the duration of the trial. Bim/Bim indicates subjects receiving bimatoprost for 12 months. Bim/Veh indicates subjects receiving bimatoprost for 6 months followed by vehicle for 6 months.

Figure 9:
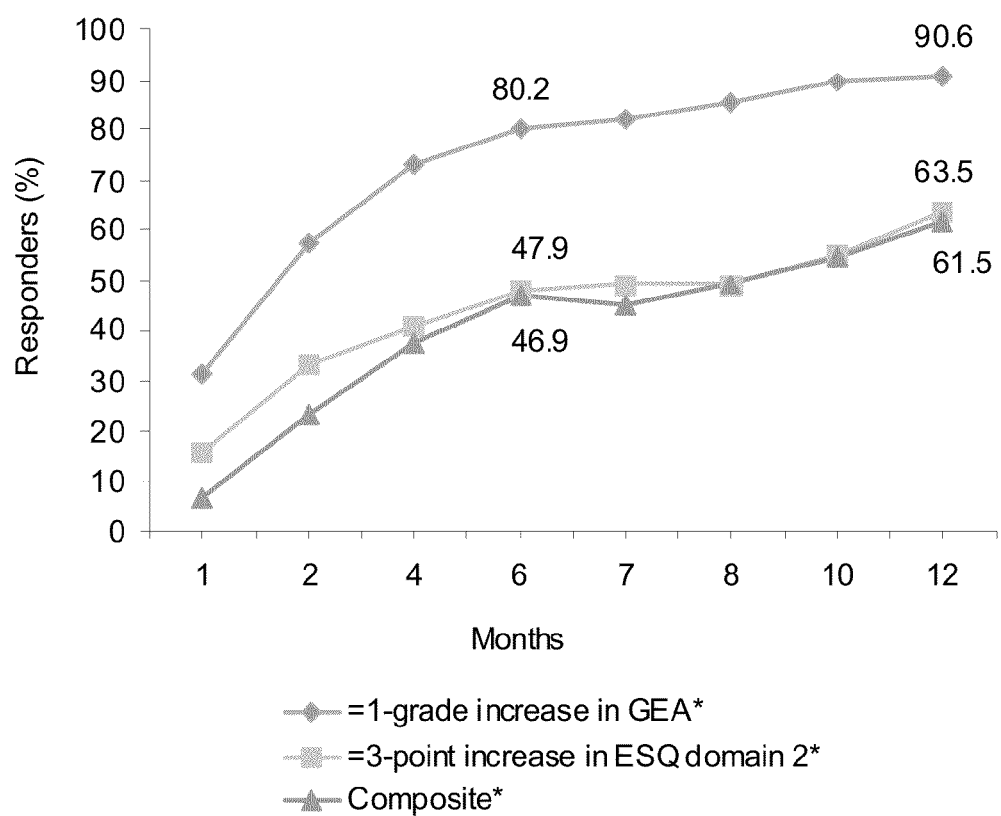
FIG. 9 is a plot of responder rates in bimatoprost-treated subjects by individual components of the primary composite efficacy measure for the duration of the trial for subjects with chemotherapy-induced hypotrichosis; and, FIG. 10 is a plot of improvement in eyelash length for the duration of the trial for subjects with chemotherapy-induced hyopotrichosis.

FIG. 9 is a plot of responder rates in bimatoprost-treated subjects by individual components of the primary composite efficacy measure for the duration of the trial. FIG. 9 shows a GEA response rate of about 80% that is similar to the idiopathic population, and continuous improvement up to month 12.

Figure 10:
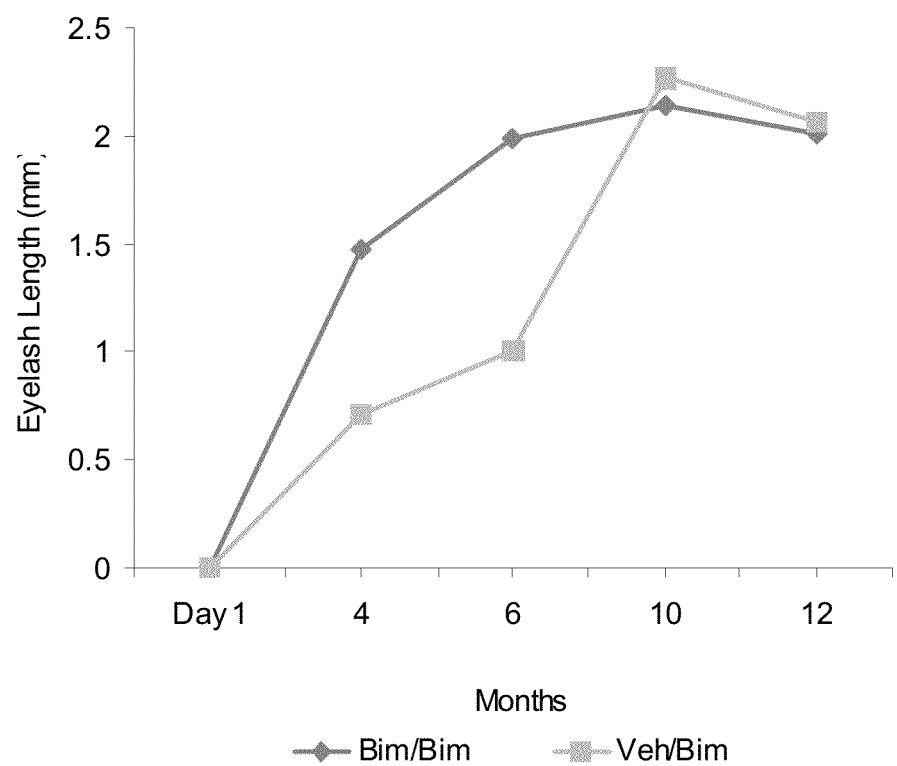

FIG. 10 is a plot of improvement in eyelash length for the duration of the trial. Bim/Bim indicates subjects receiving bimatoprost for 12 months. Bim/Veh indicates subjects receiving bimatoprost for 6 months followed by vehicle for 6 months.

Over 12 months of bimatoprost treatment, the most common adverse events (>5%) in either idiopathic or post-chemotherapy population were conjunctival hyperaemia, punctate keratitis, eyelid pruritus, erythema of eyelids, and eye pruritus. Common adverse events (conjunctival hyperaemia, punctate keratitis, and eye pruritus) were reported at a higher rate in the post-chemotherapy population. This may have been related to the enduring effect of chemotherapy drugs on eyes. Common ocular and dermal adverse events occurred at a lower rate in the second 6-month trial period (months 6-12) compared with the first 6-month trial period. No drug-related serious adverse occurred in either subpopulation.

| 0 to 12 Months | | 0 to 6 Months | | 6 to 12 Months | |
|---|---|---|---|---|---|
| Idiopathic Hypotrichosis | Post-Chemotherapy | Idiopathic Hypotrichosis | Post-Chemotherapy | Idiopathic Hypotrichosis | Post-Chemotherapy |
| (N = 118) | (N = 96) | (N = 118) | (N = 96) | (N = 106) | (N = 89) |
| Eye disorders, n (%) | | | | | |
| Conjunctival hyperaemia | 10 (8.5) | 16 (16.7) | 7 (5.9) | 15 (15.6) | 4 (3.8) | 1 (1.1) |
| Punctate keratitis | 3 (2.5) | 9 (9.4) | 3 (2.5) | 8 (8.3) | 0 (0.0) | 1 (1.1) |
| Eyelids pruritus | 7 (5.9) | 3 (3.1) | 6 (5.1) | 3 (3.1) | 1 (0.9) | 1 (1.1) |
| Erythema of eyelid | 6 (5.1) | 3 (3.1) | 2 (1.7) | 1 (1.0) | 5 (4.7) | 2 (2.2) |
| Eye pruritus | 1 (0.8) | 6 (6.3) | 1 (0.8) | 5 (5.2) | 0 (0.0) | 1 (1.1) |
| Skin and subcutaneous disorders, n (%) | | | | | |
| Skin hyperpigmentation | 2 (1.7) | 5 (5.2) | 0 (0.0) | 3 (3.1) | 2 (1.9) | 2 (2.2) |

Conclusions:

Bimatoprost ophthalmic solution 0.03% significantly increased eyelash growth in subjects with idiopathic as well as chemotherapy-induced hypotrichosis as measured by the primary composite endpoint (>1-grade increase in the GEA score AND at least 3-point improvement in ESQ domain-2 score at week 16) and all secondary endpoints (eyelash length, thickness/fullness, and darkness). Bimatoprost treatment effects were maintained through the 12-month trial period. Bimatoprost treatment was safe and well-tolerated in the 2 populations. No new safety signals were detected in the 6- to 12-month trial period. Fewer common ocular and dermal AEs occurred in the second 6-month period than in the first 6 months of bimatoprost treatment. Efficacy was maintained for about 2 months after bimatoprost discontinuation; return to near pre-treatment levels occurred at about 4 to 6 months after discontinuation. Thus, daily application of bimatoprost ophthalmic solution to the eyelid margin over a one-year period was found to be safe, well tolerated and effective in both idiopathic and post-chemotherapy populations as assessed by several safety and efficacy measures.

What is claimed is:

1. A method of increasing hair growth in chemotherapy patients, the method comprising applying bimatoprost to one selected from the group consisting of eyelids, eyebrows and the scalp before, during, or after chemotherapeutic treatment.

2. The method of claim 1, wherein bimatoprost is 0.03% w/v bimatoprost and is applied at least once a day to the eyelids.

3. The method of claim 2, wherein the method results in eyelashes which are longer, thicker or darker compared to patients receiving no treatment.

4. The method of claim 2, wherein the method is applied for at least 6 months after completing chemotherapeutic treatment.

5. The method of claim 4, wherein the method is applied for at least 12 months after completing chemotherapeutic treatment.

6. The method of claim 3, wherein the number of eyelashes increases in comparison to post-chemotherapeutic patients who received no treatment.

7. The method of claim 1, wherein the bimatoprost is added during and after post-chemotherapeutic treatment.

8. The method of claim 2, wherein the method is applied twice a day.

9. The method of claim 8, wherein the bimatoprost is applied to the upper and lower eyelid margin of each eye.

10. The method of claim 1, wherein the method effectively treats post-chemotherapeutic hair loss.

11. The method of claim 1, further comprising the step of administering one selected from the group consisting of minoxidil and Propecia®.

12. A method of preventing loss of eyelashes in patients undergoing a chemotherapeutic treatment, the method comprising applying bimatoprost to the eyelids before, during, or after chemotherapeutic treatment.

13. The method of claim 12, wherein bimatoprost is 0.03% w/v bimatoprost and the 0.03% w/v bimatoprost is applied at least once a day.

14. The method of claim 12, wherein the method results in less eyelash loss compared to patients receiving no treatment.

15. The method of claim 14, wherein the method is applied for at least 6 months after completing chemotherapeutic treatment.

16. The method of claim 14, wherein the method is applied for at least 12 months after completing chemotherapeutic treatment.

17. The method of claim 12, wherein the method is applied prior to receiving chemotherapeutic treatment.

18. The method of claim 17, wherein the method is applied for three months prior to receiving chemotherapeutic treatment.

19. The method of claim 12 wherein the bimatoprost is in the form of a solution or an emulsion.

20. The method of claim 12 wherein the bimatoprost is applied to the upper eyelid, the lower eyelid or both the upper and lower eyelid.

* * * * *